US007087578B2

(12) United States Patent
Fisher et al.

(10) Patent No.: US 7,087,578 B2
(45) Date of Patent: Aug. 8, 2006

(54) FORMULATIONS AND METHODS FOR TREATING HYPERCOAGULABLE STATES

(75) Inventors: Charles Jack Fisher, Lake Bluff, IL (US); Brian Paul Barrett, Zionsville, IN (US); Sau-Chi Betty Yan, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 470 days.

(21) Appl. No.: 10/276,771

(22) PCT Filed: May 14, 2001

(86) PCT No.: PCT/US01/11771

§ 371 (c)(1),
(2), (4) Date: Nov. 19, 2002

(87) PCT Pub. No.: WO01/89558

PCT Pub. Date: Nov. 29, 2001

(65) Prior Publication Data

US 2003/0211969 A1    Nov. 13, 2003

Related U.S. Application Data

(60) Provisional application No. 60/206,733, filed on May 24, 2000.

(51) Int. Cl.
*A61K 38/00* (2006.01)
(52) U.S. Cl. .............................. 514/21; 514/2
(58) Field of Classification Search ............ 514/2, 514/21
See application file for complete search history.

(56) References Cited

U.S. PATENT DOCUMENTS

| | | | |
|---|---|---|---|
| 4,775,624 A | 10/1988 | Bang et al. |
| 4,849,403 A | 7/1989 | Stocker et al. |
| 4,877,608 A | 10/1989 | Lee et al. |
| 4,981,952 A | 1/1991 | Yan |
| 4,992,373 A | 2/1991 | Bang et al. |
| 5,009,889 A | 4/1991 | Taylor et al. |
| 5,084,273 A | 1/1992 | Hirahara |
| 5,084,274 A | 1/1992 | Griffin et al. |
| 5,093,117 A | 3/1992 | Lawrence et al. |
| 5,112,949 A | 5/1992 | Vukovich |
| 5,175,087 A | 12/1992 | Ranby et al. |
| 5,358,932 A | 10/1994 | Foster et al. |
| 5,395,923 A | 3/1995 | Bui-Khac et al. |
| 5,413,732 A | 5/1995 | Buhl et al. |
| 5,442,064 A | 8/1995 | Pieper et al. |
| 5,453,523 A | 9/1995 | Griffith et al. |
| 5,478,558 A | 12/1995 | Eibl et al. |
| 5,516,650 A | 5/1996 | Foster et al. |
| 5,831,025 A | 11/1998 | Ogata et al. |
| 5,962,299 A | 10/1999 | Miyata et al. |
| 6,008,199 A | 12/1999 | Grinnell |
| 6,156,734 A | 12/2000 | Grinnell |
| 6,159,468 A | 12/2000 | Carlson et al. |
| 6,162,629 A | 12/2000 | Baker |
| 6,268,344 B1 | 7/2001 | Grinnell |
| 6,395,270 B1 | 5/2002 | Carlson et al. |
| 6,436,397 B1 | 8/2002 | Baker et al. |
| 6,489,296 B1 | 12/2002 | Grinnell et al. |

FOREIGN PATENT DOCUMENTS

| | | |
|---|---|---|
| DE | 3823519 | 1/1990 |
| EP | 314 095 | 10/1988 |
| EP | 315 968 B2 | 11/1988 |
| EP | 318 201 | 11/1988 |
| EP | 326 014 | 1/1989 |
| EP | 357 296 | 8/1989 |
| EP | 445 939 | 2/1991 |
| EP | 726 076 B1 | 10/1994 |
| EP | 662 513 | 1/1995 |
| EP | 0 875 252 | 11/1998 |
| JP | 01226900 | 9/1989 |
| JP | 7097335 A | 4/1995 |
| JP | 07165605 | 6/1995 |
| JP | 8301786 | 11/1996 |
| JP | 8325161 A | 12/1996 |
| WO | WO 91/12320 | 2/1991 |
| WO | WO 95/11966 | 4/1995 |
| WO | WO 97/20043 | 6/1997 |
| WO | WO 98/48818 | 11/1998 |

OTHER PUBLICATIONS

U.S. Appl. No. 09/545,175, filed Apr. 6, 2000.
Natanson, et al. "Anti-Inflammatory Therapies to Treat Sepsis and Septic Shock: A Reassessment", Crit. Care Med. 25:1095-1100, 1997.
Barbour, et al., "Controversies in Thromboembolic Disease During Pregnancy: A Critical Review", Obstet. Gynecol. 86(4):621-633, 1995.
Bazarbachi, et al., "Changes in Protein C, Factor VII and Endothelial markers After Autologous Bone Marrow Transplantation: Possible Implications in the Pathogenesis of Veno-Occlusive Disease," Nouv Rev Fr Hematol 35:135-140,1993.
Blamey, et al., "Protein C Antigen Levels in Major Abdominal Surgery:Relationships to Deep Vein Thrombosis, Malignancy and Treatment with Stanozolol", Thromb. Haemost. 54:622-625, 1985.
Butler, et al., "*Yersinia pestis* Infection in Vietman. I. Clinical and Hematologic Aspects", The Journal of Infectious Disease 129:S78-S84; 1974.

(Continued)

*Primary Examiner*—Jean C. Witz
(74) *Attorney, Agent, or Firm*—Danica Hostettler

(57)    ABSTRACT

A method of treating a human patient with a hypercoagulable state or protein C deficiency, which comprises administering activated Protein C and protein C Zymogen.

37 Claims, No Drawings

OTHER PUBLICATIONS

Carpenter, et al., Purpura Fulminans in Pneumococcal Sepsis: Case Report and Review', Scand J Infect Dis 29:479-483, 1997.

Collins, et al., "Factor VIIa and Other Haemostatic Variables Following Bone Marrow Transplantation", Throm. And Haemo. 72:28-32, 1994.

Collins, et al., "Pitfalls in Peripheral Vascular Surgery: Disseminated Intravascular Coagulation", Am. J. Surgery 124:375-380, 1977.

Conrad, et al., "Thrombosis and Pregnancy in Congenital Deficiencies in AT III, Protein C or Protein S: Study of 78 Women", Throm. Haemost. 63 (2) :319-320, 1990.

Curreri, et al., "Coagulation Dynamics Following Thermal Injury", Ann.Surc. 181:161-163, 1974.

Dahlback, et al., "Inherited Thrombophilia: Resistance to Activated Protein C as a Pathogenic Factor of Venous Thromboembolism", Blood 85(3):607-614, 1995.

Database Medline, AN91073823, Pyzh M.V., et al., "Effects of low doses of activated protein C in experimental arterial thrombosis in rats", XP002069505 abstract.

De Stefano, et al., "Thrombotic Risk During Pregnancy and Puerperium in Woman with APC-Resistance—Effective Subcutaneous Heparin Prophylaxis lin a Pregnancy Patient", ThrombHaemost 74:793-794, 1995.

Esmon, "The Protein C Anticoagulant Pathway", Arteriosclerosis & Thromb. 12:135-145, 1992.

Esmon, C.T., "The Regulation of Natural Anticoagulant Pathways" Science, vol. 235, pp. 1348-1352 (Mar. 1987).

Faioni, et al., "Naturally Occurring Anticoagulants and Bone Marrow Transplantation: Plasma Protein C Predicts the Development of Venocclusive Disease of the Liver," Blood 81:3458-3462, 1993.

Fourrier, et al., "Septic Shock, Multiple Organ Failure, and Disseminated Intravascular Coagulation", Chest 101:816-823, 1992.

Franz, et al., "Clinical Recognition and Management of Patients Exposed to Biological Warfare Agents", Journal of the American Medical Assoc. 278(5):399-411, 1997.

Gerson, et al., "Severe Acquired Protein C Deficiency in Purpura Fulminans Associated with Disseminated Intravascular Coagulation: Treatment with Protein C Concentrate", Pediatrics 91(2):418-422, 1993.

Gibaldi, Anatomy of an Antibody, and Related Misadventures in Developing an Effective Treatment for Septic Shock,, Pharmacotherapy 13(4):302-308, 1993.

Gordon, et al., "Thrombotic Complications of BMT: Association with Protein C Deficiency", Bone Marrow Transplan. 11:61-65, 1993.

Graybill, et al., "Complement and Coagulation in Rocky Mountain Spotted Fever", Southern Medical Journal 66(4):410-413, 1973.

Grinnell, et al., Trans-Activated Expression of Fully Gamma-Carboxylated Recombinant Human Protein C, an Antithrombotic Factor, Bio/Technolocay 5:1189-1192, 1987.

Haire, et al., "Multiple Organ Dysfunction Syndrome in Bone Marrow Transplantation," JAMA 274:1289-1295, 1995.

Harper, et al., "Changes in the Natural Anticoagulants Following Bone Marrow Transplantation", Bone Marrow Trans. 5:39-42, 1990.

Harper, et al., "Protein C Deficiency and Portal Thrombosis in Liver Transplantation in Children", Lancet 924-927, 1988.

Hill, et al., "Leptospiral Pneumonia", Seminars in Respiratory Infections 12(1):44-49, 1997.

Howey, et al., Preparation for Trials of Recombinant Activated Protein C in Sepsis: A pharmacoknietic and Dynamic Study in Healthy Men and Women', Chest 112(3) : 89S, 1997.

Koul, et al., Haemostatic Abnormalities in Multidrug-Resistant Enteric Fever', Acta Haematol 93:13-19, 1995.

Leclerc, J.R., "Low-Molecular Weight Heparin Prophylaxis in Surgical Patients", Clin. Appl. Thrombosis/Hemostasis 3(3):153-156, 1997.

Lercari,et al., "Apheresis for SevereMalaria Complicated by Cerebral Malaria, Acute Respiratory Distress Syndrome, Acute Renal Failure, and Disseminated Intravascular Coagulation", Journal of Clinical Apheresis 7:93-96, 1992.

Levi, et al., "Pathogenesis of Disseminated Intravascular Coagulation in Sepsis", JAMA 270:975-979, 1993.

Levin, "Syndromes with Renal Failure and Shock", Pediatric Nevhroloav 8:223-229, 1994.

Lo, et al., "Protein C and Protein S Levels in Some Burn Patients", Burns 20:186, 1994.

Loubser, et al., "Severe Illness caused by *Rickettsia conorii*", Annals of Tropical Paediatrics 13:277-280, 1993.

Maraganore, "Hirudin and Hirulog" :Advances in Antithrombotic Therapy, Perspective in Drua Discovery and Design 1:461-478, 1994.

Mayer, et al., "Coagulopathies Associated with Major Spinal Surgery", Clin. Orthop. 245:83-88, 1989.

McManus, et al., "Disseminated Intravascular Coagulation in Burned Patients", J. of Trauma 13(5):416-422, 1973.

Menges, et al., "The Role of the Protein C-Thrombomodulin System and Fibrinolysis During Cardiovascular Surgery: Influence of Actue Preoperative Plasmapheresis", J. Cariothor Vasc An. 10:482-489, 1996.

Mesters, et al., "Factor VIIa and Antithrombin III Activity During Severe Sepsis and Septic Shock in Neutropenic Patients", Blood 88: 881-886, 1996.

Murakami, et al., "Activated Protein C Attenuates Endotoxin-Induced Pulmonary Vascular Injury by Inhibiting Activated Leukocytes in Rats",Blood 87:642-647, 1996.

Natanson, et al., "Selected Treatment Strategies for Septic Shock Based on Proposed Mechanisms of Pathogenesis", Ann. Intern. Med. 120(9):771-783, 1994.

Nguyen, et al., Varicela and thrombotic complications associated with transient protein C and protein S deficiencies in children', Eur J Pediatr 153:646-649, 1994.

Okajima K., et al., "Effect of protein C and activated protein C on coagulation and fibrinolysis in normal human subjects" Thrombosis and Haemostasis, 63(1):48-53, 1990.

Okajima, et al., "Treatment of Patients with Disseminated Intravascular Coagulation by Protein C", Amer. J. of Hematology 33:277-278, 1990.

Okamoto, et al., Protective/Effect of Neutrophil Elastase Inhibitor (EI) and Activated Protein C (APC) on the Organ Failure and Coagulopathy in Cecal Ligation and Puncture (CLP) Sepsis in the Rabbit', Gastroenterology 106:A747, 1994.

OTA, "Successful Treatment of Severe Odontogenic Infections which caused Septicemia", Y..J. Japanese Assoc. Infec. Dis. 68:157-161, 1994.

Parrillo, "Pathogenetic Mechanisms of Septic Shock", N. Enal. J. Med. 328 (20):1471-1477, 1993.

Patent Abstracts of Japan 18(528) (C-1258), Oct. 6, 1994 & JP 06183996 A (Chemo sero Therapeut Res Inst) Jul. 5, 1994 abstract.

Perry, et al., "Abnormal Hemostasis and Coagulopathy in Preeclampsia and Eclampsia", Clin. Obstet. Gynecol. 35:338-350, 1992.

Powars, et al., "Epidemic Meningococcemia and Purpura Fulminans with Induced Protein C Deficiency", Clin. Infectious Diseases 17:254-261, 1993.

Puthucheary, et al., "Septicaemic meliodosis: a review of 50 cases from Malaysia", Transactions of the Royal Society of Trovical Medicine and Hvaiene 86:683-685, 1992.

Rathgeber, et ' al., "Anesthesiological and Intensive Care Medicine Aspects of Severe Preeclampsia with HELLP Syndrome", Anasth Intensivther Notfallmed 25:206-211, 1990.

Rintala, et al., "Protein C in the Treatment of Coagulopathy in Meningococcal Disease", Lancet 347:1767, 1996.

Rivard, et al., "Treatment of Purpura Fulminans in Meningococcemia with Protein C Concentrate", J. Pediatr. 126:646-652, 1995.

Segel, I., "Enzyme Kinetics" (1975) Wiley Interscience, New York, pp. 884-896.

Smith, et al., "Successful Treatment of Meningoccal Induced Protein C Deficiency/Purpura Fulminans in Children with Protein C Concentrate and Heparin", Thromb. Haemost, PS1709, p. 419, 1997.

Smith, et al., "Use of Protein-C Concentrate, Heparin and Haemodiafiltration in Meningococcus-Induced Purpura Fulminans", The Lancet 350:1590-1593, 1997.

Sorenson, et al., Protein C in Renal Allotransplantation during the Perioperative Period', J. Inter. Med. 226:101-105, 1989.

S. A. Steiner, et al. Stimulation of the Amidase and Esterase Activity of Activated Bovine Plasma Protein C by Monovalent Cations' Biochemical and Biophvsical Research Communications 94(1):340-347 (May 14, 1980).

Taylor, et al., DEGR-Factor XA Blocks Disseminated Intravascular Coagulation Initiated by *Escherichia coli* Without Preventing Shock or Organ Damage, Blood 78:364-368, 1991.

Taylor, et al., Protein C Prevents the Coagulopathic and Lethal Effects of *Escherichia coli* Infusion in the Babod, J. Clin. Invest. 79:918-925, 1987.

Thomas, et al., "Primary Hypercoagulable States in General and Vascular Surgery", Am. J. Surgery 158:491-494, 1989.

Ueyama, et al., Nippon Geka Gakki Zasshi 92:907-12, 1991.

Uzan, et al., "Pathophysiological Aspects of Preeclampsia and the Place of the Principal Additional Examinations", Rev. Fr. Gvnecol.Obstet. 86:158-163, 1991.

Veldman, et al., "A New Option in the Treatment of VOD After BMT: Continuous Infusion of Recombinant Tissue Plasminogen Activator and Protein C", Bone Marrow Trans. 21:S238, 1998.

Veldman, et al., "Treatment of DIC in Septic Shock with Protein C Concentrate", Blood 90:3271, 1997.

Watkins, et al., "The Early Diagnosis of Impending Coagulopathies Following Surgery and Multiople Trauma", Klin Worchenschr 63:1019-1027, 1985.

Yu-Chang, J.W. and Hanson Ma (1988) Parenteral Formulations of Proteins and Peptides: Stability and Stabilizers, Journal of Parenteral Science and Technology 42(Supp): S-S26.

Zeffren et al., "The Study of Enzyme Mechanisms" (1973) John Wiley & Sons, New York, p. 84.

FORMULATIONS AND METHODS FOR TREATING HYPERCOAGULABLE STATES

This is the national phase application, under 35 USC 371, for PCT/US01/11771, filed 14 May 2001, which claims the priority of U.S. provisional application No. 60/206,733, filed 24 May 2000.

This invention relates to methods for treating vascular occlusive disorders and hypercoagulable states, including sepsis, disseminated intravascular coagulation, purpura fulminans, major trauma, surgery, burns, adult respiratory distress syndrome (ARDS), transplantations, deep vein thrombosis, heparin-induced thrombocytopenia, sickle cell disease, thalassemia, viral hemorrhagic fever, thrombotic thrombocytopenic purpura, hemolytic uremic syndrome, acute coronary syndromes (ACS; e.g. unstable angina, myocardial infarction) and protein C deficiency characterized by administering a combination of activated Protein C (aPC or APC) and protein C zymogen (PCZ). The invention also includes inventive formulations comprising aPC, PCZ and a pharmaceutically acceptable carrier.

Protein C is a serine protease and naturally occurring anti-coagulant produced as an inactive precursor or zymogen by the liver. Human protein C is made in vivo as a single polypeptide of 461 amino acids. This polypeptide undergoes multiple post-translational modifications including: 1) cleavage of a 42 amino acid signal sequence; 2) cleavage of lysine and arginine residues (positions 156 and 157) to make a 2-chain inactive zymogen (a 155 amino acid residue light chain attached via a disulfide bridge to a 262 amino acid residue heavy chain); 3) vitamin K-dependent carboxylation of nine glutamic acid residues located within the amino-terminal 45 residues (gla-domain); and, 4) carbohydrate attachment at four sites (one in the light chain and three in the heavy chain). The protein C zymogen circulates in the plasma and, upon removal of a dodecapeptide at the N-terminus of the heavy chain, results in aPC possessing enzymatic activity. aPC plays a key role in regulating hemostasis by inactivating Factors $V_a$ and $VIII_a$ in the coagulation cascade.

Blood coagulation is a highly complex process regulated by the balance between pro-coagulant, anti-coagulant, and fibrinolytic mechanisms. This balance determines a condition of either normal hemostasis or abnormal pathological thrombus generation and the progression of hypercoagulable states. Two major factors control this balance; the generation of fibrin and the activation and subsequent aggregation of platelets, both processes controlled by the generation of the enzyme thrombin, which occurs following activation of the clotting cascade. Thrombin, in complex with thrombomodulin, also functions as a potent anti-coagulant since it activates protein C zymogen to the active enzyme, aPC. In large blood vessels, the activation of protein C zymogen to aPC by thrombin-thrombomodulin complex is further augmented by an endothelial transmembrane protein, endothelial-protein receptor (EPCR) [Stearn-Kurosawa, et al. *Proc. Natl. Acad. Sci. USA* 93:10212–10216, 1996]. APC, in turn inhibits the generation of thrombin. Thus, through the feedback regulation of thrombin generation via the inactivation of Factors Va and VIIIa, aPC functions as perhaps the most important down-regulator of blood coagulation resulting in protection against thrombosis.

Additionally, aPC exerts profibrinolytic properties that facilitate clot lysis and exerts anti-inflammatory effects via inhibiting the release of inflammatory mediators, such as, tumor necrosis factor and various interleukins.

Recombinant aPC has completed Phase III clinical trials for treating severe sepsis. In addition, Phase III studies directed to the use of plasma derived human aPC in DIC, where severe sepsis is a subset of the patients studied, have been completed in Japan. The use of aPC to treat congenital and acquired protein C deficiency and to treat disseminated intravascular coagulation (DIC) and hypercoagulopathy have also been reported. Wada, et al., 1993, *Am. J. Hematol.* 44:218–219; Sugimoto, et al., 1997, *Thromb. Haemost.* 77:1223–1224; Oh, et al., 1998, *Blood,* 92:4402; Aoki, et al., 1998, *J. New Remedies & Clinics* 47:448–482).

Several encouraging pre-clinical studies using aPC in animal models have also been reported. A study in a baboon sepsis model by Taylor, et al., [*J. Clin. Invest.* 79:918–25, 1987], used plasma-derived human aPC. Five out of five animals survived 7 days and were considered permanent survivors to the experimental protocol. In control animals receiving an identical infusion of *E. coli*, five out of five animals died in 24 to 32 hours. The use of recombinant aPC for treating thrombotic occlusion or thromboembolism in a baboon model was also disclosed by Griffin, et al. in U.S. Pat. No. 5,084,274 and European Patent Application EP 0 318 201 B1.

In a lipopolysaccharide (LPS; *E. coli*) sepsis model in rats [Murakami, et al., *Blood* 87:642–647, 1996], the pulmonary vascular injury induced by LPS was inhibited by human plasma-derived aPC. Furthermore, in a ligation and puncture sepsis model in rabbits, Okamoto, et al., [*Gastroenterology* 106:A747, 1994], demonstrated that plasma-derived human aPC was effective in protecting the animals from coagulopathy and organ failure.

Plasma derived PCZ is approved for treating congenital protein C deficiency in both Europe and Japan. The use of human PCZ to treat congenital and acquired protein C deficient states has also been reported. See: (e.g. Dreyfus, et al., *Semin. Thromb. Hemost.* 21:371–381, 1995; Minford, et al., *Br. J. Haematol.,* 93:215–216, 1996; Smith, et al., *Lancet,* 350:1590–1593, 1997). In addition, plasma-derived human PCZ has been used as a successful adjunct to aggressive conventional therapy in the management of forty-seven patients with purpura fulminans in bacterial sepsis of which forty survived (Gerson, et al., *Pediatrics* 91:418–422, 1993; Smith, et al., *Lancet* 350:1590–1593, 1997; White, et al., *Blood* 92:670a #2765, 1998; Ettingshausen, et al., *Semin. Thromb. Hemost.* 25:537–541, 1999; Betrosian, et al., *Crit. Care Med.* 27:2849–2850, 1999; Rintala, et al., *Lancet* 347:1767, 1996; Rivard, et al., *J. Pediatr.* 126:646–652, 1995). Gerson, et al., [1993] describe treatment of a child with proven gram positive bacteremia and purpura fulminans, who was failing to respond to aggressive conventional treatment. The patient was treated with plasma-derived human PCZ resulting in an associated correction of coagulopathy and DIC, and arrest of clinical signs of the development of septic shock-related purpura fulminans.

Rintala, et al., [1996] reported the treatment of 2 adults with meningococcal septicemia presented with purpura fulminans. The patients were treated with plasma-derived PCZ at 400 µg/kg bolus every six hours for 8–10 days. One died and one survived. Rivard, et al., [1995] reported the treatment of four patients with meningococcemia and purpura fulminans, who all survived following human PCZ therapy. Smith, et al., [1997] and White, et al., [1998] treated thirty patients with meningococcemia with plasma-derived PCZ at about 400 µg/kg bolus followed by 60 µg/kg/hour infusion for several days. Twenty-seven of the thirty patients survived. Ettingshausen, et al., [1999] treated eight meningococcemia patients with plasma-derived PCZ at a bolus of about 320–480 µg/kg followed by about 200 µg/kg up to once every 4 hours. Median treatment time was three days and the range was from one to sixteen days. Six of the eight patients survived. Betrosian, et al., [1999] treated one patient with meningococcemia with plasma-derived PCZ at 400 µg/kg every 6 hours the first day and 240 µg/kg every six hours the subsequent two days. The patient did not survive.

Plasma-derived human PCZ has also been reported to successfully treat other hypercoagulable or acquired protein C deficient states such as veno-occlusive disease as a complication of bone marrow transplantation (Veldman, et al., *Bone Marrow Transplant.* 21:S238, 1998), devastating coagulopathy of unknown etiology (Favier, et al., *Hematol. Cell Therapy* 40:67–70, 1998), and heparin-induced thrombocytopenia (Boshkov, et al., *Blood* 94:102b, 1999).

PCZ and aPC differ structurally and also differ pharmacokinetically and pharmacodynamically. PCZ is a pharmaceutically inactive protein and in humans is present in concentrations of about 4 µg/ml. PCZ is converted to aPC by thrombin in complex with an endothelial membrane protein, thrombomodulin in the microvascular beds. In larger blood vessels, the conversion of PCZ to aPC is further facilitated by EPCR in complex with thrombin-thrombomodulin. Therefore, aPC prolongs aPTT clotting time in treated subjects while PCZ does not. APC also circulates in humans at a much lower concentration of about 2 ng/ml. APC has a half-life in humans of about 23–45 minutes, more than 10 fold shorter than the PCZ (approximately 10 hours). *Shock*, Vol. 12, No. 3, 243–244, 1999. One reason for the short half-life is that blood levels of aPC are regulated by molecules known as serpins (Serine Protease Inhibitors), which covalently bind to aPC forming an inactive serpin/aPC complex. The serpin/aPC complexes are formed when aPC binds and proteolytically cleaves a reactive site loop within the serpin; upon cleavage, the serpin undergoes a conformational change irreversibly inactivating aPC. The serpin/aPC complex is then eliminated from the bloodstream primarily via hepatic receptors for the serpin/aPC complex.

A major lesson from various studies is that early intervention in treating hypercoagulable states, such as sepsis, is more likely to succeed. Evidence is suggesting that the earlier the therapeutic intervention relative to the inflammatory challenge, the more likely that a drug will have a beneficial effect. Dellinger, et al., *Chest,* 1997, 111:744–53. Toshiaki, et al., *J Am Coll Surg,* 1998, 187: 321–329. (Early diagnosis is now considered critical in severe sepsis . . . Because treatment has poor results when begun in the later stages of sepsis, treatment should be started as soon as possible).

Although early therapeutic intervention is preferred, for a variety of medical reason (e.g., potential adverse effects and drug interactions), it is often undesirable to treat a patient with aPC prior to confirmation of a hypercoagulable or protein C deficient state. In addition, disadvantages of treatment with PCZ alone also exist. For example, it takes time to convert the inactive PCZ to the active and useful aPC. Furthermore, some patients may be unable, or have a reduced capacity, to convert PCZ to aPC. For example, certain cytokines released into the circulation during hypercoagulable states may down-regulate the amount of thrombomodulin on endothelial cell surfaces and thus, impede the rate of protein C activation (Moore, et al., *Blood* 73:159–165, 1989). Faust, et al., also report that the molecular machinery needed to convert PCZ to aPC is down-regulated in septic patients. *Shock* 2000: 13 (Suppl.):29 (abst.#12). Moreover, aPC may be more resistant to neutrophil elastase than PCZ (Philapitsch, et al., *Thromb. Haemost,* 69:A664, 1993). Elastase is elevated in sepsis (Setiz, et al., *Eur. J. Haematol.* 43:22–28, 1989; Jansen, et al., *Blood* 87:2337–2344, 1996). Therefore, administration of aPC alone and administration of PCZ alone may result in less than optimal treatment of hypercoagulable states and/or protein C deficient states.

The present invention is the first to describe the combination of aPC and PCZ in the treatment of hypercoagulable states and/or protein C deficiency. The combination of aPC and PCZ results in a treatment that allows for the reduction of the dosages of both aPC and PCZ and an improvement of clinical treatment options and outcome of the patient being treated. Reducing the amount of an agent in this combination therapy may result in reduced side effects that may occur with either agent, particularly with the potential for bleeding that may be induced by administering a higher dose of aPC. This combination is particularly preferred for those patients prone to bleeding episodes or at high risk of bleeding, for example, due to inherited bleeding disorders and/or for patients taking therapeutic agents that may increase the risk of bleeding episodes. This combination also allows for a more rapid treatment approach (PCZ) followed by administration of aPC upon confirmation of a protein C deficient state and/or a hypercoagulable state or when a clinician suspects a patient may be unable to convert PCZ to the active form of the protein, aPC.

The combination therapy of PCZ and aPC may be administered in any sequence or combination according to the best combination for a particular patient or disease need. The present invention is intended to encompass all dosing regimens employing aPC and PCZ for preventing or treating a condition disclosed herein. The needs of a particular patient and the preferences of a treating physician may result in aPC and PCZ being used in a variety of dosing schedules. For example, PCZ may be administered prior to aPC. APC may be administered prior to PCZ. PCZ and aPC may also be administered simultaneously at different combination proportions. PCZ and aPC may also be administered with varying doses and alternating back and forth between the two agents. The following are examples of possible dosing options and are not intended to limit the scope of the invention in any way. PCZ and aPC are preferably administered parenterally, for example, by an intravenous or subcutaneous route. PCZ and aPC may also be administered in bolus, loading dose, or continuous infusion.

PCZ administered before aPC: for patients that are at high risk of developing sepsis, for example, PCZ may be given prophylactically to prevent the patients from developing sepsis or severe sepsis. As explained in more detail below, patients at greater risk of developing sepsis include patients with cancer who are undergoing chemotherapy; patients undergoing other trauma or surgeries, such as, abdominal surgeries or an organ transplantation; severely burned patients; and pregnant patients. For example, it is known that protein C levels can decrease to 40% of normal level in neutropenic patients (cancer patients that were treated with intense chemotherapy) some 12 hours before the onset of clinical symptoms of septic shock. Mesters, et al., *Crit. Care Med.,* in press). The low level of protein C in this group of patients was predictive of the mortality outcome of the patients. This group of patients that showed this dramatic drop in protein C all died. Those that did not have this drop of protein C survived. So the physicians that are caring for patients that are at high risk of developing sepsis can monitor the level of protein C. As soon as protein C starts to decrease below a normal level, the physician can administer PCZ to the patient. PCZ can be given subcutaneously (for example, at a dose of (about 200–2000 µg/kg) once a day to once every 2–3 days depending on the protein C consumption rate to maintain the endogenous PCZ level at about 100% of normal or intravenously at a dose of about 200–700 µg/kg once a day. This prophylactic treatment with PCZ may reduce the development and/or severity of severe sepsis. APC is then administered to treat the patient upon development of sepsis, severe sepsis, or septic shock.

APC during the acute phase of severe sepsis and septic shock is considered better treatment than PCZ because, as previously stated, thrombomodulin, which is required to convert PCZ to aPC in the patient may be down-regulated due to inflammation during sepsis (Moore, et al. 1989). Also, PCZ is more susceptible to degradation by neutrophil elastase than aPC (Philapitsch, et al., *Thromb. Haemost*, 69:A664, 1993). Circulating neutrophil elastase is elevated during severe sepsis.

After treating the patient with aPC for about 1 to about 10 days or until the patient's endogenous protein C level is near the normal level, the physician may again administer PCZ (and continue or discontinue the aPC) for a period of time until all signs of coagulopathy are resolved. Patients who may need this last stage of PCZ treatment may be patients who developed purpura fulminans during the severe sepsis/septic shock stage. There may be necrotic tissues or digits that may need skin grafting or amputation. The ischemic tissues that are beyond salvage may continue to induce low-grade coagulopathy until the proper procedures are performed. Other patients who may benefit from the above-described dosage regimen include patients who suffer from trauma, burns or patients undergoing or who are about to undergo organ transplantation and those patients developing veno-occlusive disease.

aPC given before PCZ: for a patient presenting to the hospital or physician with obvious symptoms of a hypercoagulable state, for example, severe sepsis or septic shock, these patients may be treated immediately with aPC for about 1 to about 10 days or until the patient's endogenous protein C level is above the lower limit of the normal range (the lower limit of normal is about 60–80%, as described in more detail herein). An example of this scenario is a patient presenting with purpura fulminans from either gram negative or gram positive bacteremia, or viral or parasitic infection. This patient will be treated with aPC first, for example, at a dose of about 10 µg/kg/hr to about 36 µg/kg/hr for about 1 to about 10 days followed by treatment with PCZ at a dose of (200–600 µg/kg once a day) for an additional period of 1 to about 7 days, up to several weeks. An additional example is directed to treating a patient who presents with an acute phase of melioidosis. The patient will be treated with aPC, for example, at a dose of about 10 µg/kg/hr to about 36 µg/kg/hr for 1 to about 10 days (with or without an initial aPC bolus). In that the pathogen that causes melioidosis, *B. pseudomallei*, requires 2 weeks to 6 months of anti-infective treatment for total disease remission, *B. pseudomallei* may be actively infecting the patient for up to 6 months. This may result in a continuous or "chronic" acquired protein C deficiency requiring treatment with PCZ for up to 6 months. The actual doses of aPC and PCZ may be varied to ultimately achieve activated Protein C plasma levels in the range of 2 ng/ml to 200 ng/ml, preferably in the range of 10 ng/ml to 90 ng/ml. Another example is directed to treating a patient that is first diagnosed with congenital protein C deficiency presenting with acute purpura fulminans or a patient with congenital protein C deficiency suffering from an acute crisis of thrombosis/hypercoagulopathy. This patient will be treated with aPC first, for example, at a dose of about 10 µg/kg/hr to about 36 µg/kg/hr for about 1 to about 10 days followed by treatment with PCZ at a dose of (200–600 µg/kg once a day) for an additional period of 1 to about 7 days, up to several weeks. One or two days into PCZ therapy, chronic anti-coagulant therapy can be initiated while the PCZ therapy can be gradually weaned. Example of chronic anti-coagulant therapy can be oral wafarin therapy, or heparin therapy (low-molecular weight heparin or unfractionated heparin given intravenously or subcutaneously). These patients generally require chronic anti-coagulant therapy for life. PCZ and aPC can be life-saving for this group of patients during acute thrombotic crisis.

Monitoring PCZ and aPC may be conducted by various methods, including an enzyme capture immunogenic method for measuring aPC levels; other methodologies that are in development for measuring PCZ levels such as a combination of antigenicity and mass spectrometric method; and preferably by commercially and clinically approved diagnostic kits for PCZ measurements using antigenicity or activity methodologies.

aPC and PCZ given simultaneously: In the above two scenarios, it may be difficult to determine precisely when to transition from administering PCZ to administering aPC or vice versa. So during the transition, the physician may use aPC and PCZ together before transition into PCZ or aPC therapy alone. In addition, a physician may decide to reduce the dose of either aPC or PCZ for a variety of reasons. A patient may be at an increased risk of bleeding with aPC and lowering the aPC dose while continuously administering PCZ may benefit the patient's hypercoagulable state and/or protein C deficiency. A physician may want to administer a lower dose of aPC, for example, 5 µg/kg/hr to about 20 µg/kg/hr simultaneously with, for example, 20–100 µg/kg of PCZ by bolus while determining whether the patient has the ability to convert PCZ to aPC in vivo.

Examples of certain hypercoagulable states contemplated within the scope of this invention are described below.

Sepsis

Sepsis is defined clinically as a systemic response to infection or suspected infection complicated by one or more organ failures, sepsis is associated with and mediated by the activation of a number of host defense mechanisms including the cytokine network, leukocytes, and the complement and coagulation/fibrinolysis systems. [Mesters, et al., *Blood* 88:881–886, 1996]. Disseminated intravascular coagulation [DIC], with widespread deposition of fibrin in the microvasculature of various organs, is an early manifestation of sepsis/septic shock. DIC is an important mediator in the development of the multiple organ failure syndrome and contributes to the poor prognosis of patients with severe sepsis. [Fourrier, et al., *Chest* 101:816–823, 1992].

Blocking DIC has also been proposed as a new target for clinical trials in sepsis [e.g., Levi, et al., *JAMA* 270:975–979, 1993]. However, simply blocking the coagulation defect in sepsis may not be sufficient. As reviewed by Esmon, [*Arteriosclerosis & Thromb.* 12:135–145, 1992], several antithrombotics have not shown efficacy in the baboon sepsis model, including active site-blocked factor Xa [Taylor, et al., *Blood* 78:364–368, 1991], hirudin and hirulog [Maraganore, *Perspective in Drug Discovery and Design* 1:461–478, 1994]. Each of these antithrombotics were able to block the consumptive coagulopathy in the animals but were not able to improve survival. Additionally, investigators in Japan [patent application JP7097335A] have proposed treating coagulopathy associated with hepatic insufficiency, which has the potential of developing DIC-like symptoms, with plasma derived activated Protein C.

Purpura fulminans (ecchymotic skin lesions, fever, hypotension associated with bacterial sepsis, viral, bacterial or protozoan infections) and/or DIC have been associated with numerous bacterial, viral, or protozoan infections which include but are not limited to infections caused by *Rickettsia* (Rocky Mountain Spotted fever, tick bite fever, typhus, etc.) [Graybill, et al., *Southern Medical Journal*, 66(4):410–413, 1973; Loubser, et al., *Annals of Tropical Pediatrics* 13:277–280, 1993]; *Salmonella* (typhoid fever, rat bite fever) [Koul, et al., *Acta Haematol*, 93:13–19, 1995]; *Pneumococci* [Carpenter, et al., *Scand J Infect Dis*, 29:479–483, 1997] *Yersina pestis* (Bubonic plague) [Butler, et al., *The Journal of Infectious Disease*, 129:578–584, 1974]; *Legionella pneumophila* (Legionnaires Disease); *Plasmodium falciparum* (cerebral malaria) [Lercari, et al., *Journal of Clinical Apheresis*, 7:93–96, 1992]; *Burkholderia pseudomallei* (Melioidosis); *Pseudomonas pseudomallei* (Melioidosis) [Puthucheary, et al., *Transactions of the Royal Society of Tropical Medicine and Hygiene*, 86:683–685, 1992]; *Streptococci* (Odontogenic infections) [Ota, Y., *J. Japanese Assoc. Infect. Dis.*, 68:157–161]; zoster virus [Nguyen, et al., *Eur J Pediatr,* 153:646–649, 1994]; *Bacillus anthracis* (Anthrax) [Franz, et al., *Journal of the American Medical Assoc.*, 278(5):399–411, 1997]; *Leptospira interrogans* (leptospirosis) [Hill, et al., *Seminars in Respiratory Infections,* 12(1):44–49, 1997]; *Staphylococci* [Levin, M., *Pediatric Nephrology*, 8:223–229]; *Haemophilus aegyptius* (Brazilian purpuric fever); *Neisseria* (gonococcemia, meningococcemia); and *mycobacterium tuberculosis* (miliary tuberculosis).

Even though the purpura fulminans, DIC or acquired protein C deficiency conditions in sepsis/septic shock or other infections have been well documented as indicated above, there is no suggestion to treat these patients according to the inventive treatment methods of the present application.

Transplantation

A variety of transplantation associated thromboembolic complications may occur following bone marrow transplantation (BMT), liver, kidney, or other organ transplantations [Haire, et al., *JAMA* 274:1289–1295, (1995); Harper, et al., *Lancet* 924–927 (1988); and Sorensen, et al., *J. Inter. Med* 226:101–105 (1989); Gordon, et al., *Bone Marrow Transplan.* 11:61–65, (1993)]. Decreased levels of circulating protein C have been reported after BMT [Bazarbachi, et al., *Nouv Rev Fr Hematol* 35:135–140 (1993); Gordon, et al., *Bone Marrow Trans.* 11:61–65 (1993)], renal transplantation [Sorensen, et al., *J. Inter. Med* 226:101–105 (1989)], and liver transplantation [Harper, et al., *Lancet* 924–927(1988)]. This deficiency in protein C contributes to a hypercoagulable state placing patients at risk for thromboembolic complications.

For example, hepatic venocclusive disease (VOD) of the liver is the major dose-limiting complication of pre-transplantation regimens for BMT. VOD is presumably the result of small intrahepatic venule obliteration due to intravascular deposition of fibrin. [Faioni, et al., *Blood* 81:3458–3462 (1993)]. In addition, VOD causes considerable morbidity and mortality following BMT [Collins, et al., *Throm. and Haemo.* 72:28–33 (1994)]. A decreased level of protein C coincident with the peak incidence of VOD has been reported [Harper, et al., *Bone Marrow Trans.* 5:39–42 (1990)] and is likely to be a contributing factor to the genesis of this condition.

Organ dysfunction after BMT including pulmonary, central nervous system, hepatic or renal, is a complication that occurs in a high percentage of transplant patients [Haire, et al., *JAMA* 274:1289–1295, (1995)]. A single organ dysfunction in BMT is a strong predictor of multiple organ dysfunction syndrome (MODS) which is the leading cause of death in BMT patients. Disseminated intravascular coagulation (DIC) due to a massive activation of the coagulation system and widespread deposition of fibrin in the microvasculature of various organs is an important mediator in the development of MODS [Fourrier, et al., *Chest* 101:816–823 (1992)]. Thus, a deficiency in protein C levels in patients who have undergone bone marrow or other organ transplantations leads to a hypercoagulable state that predisposes the patients to venous thromboembolic complications and organ dysfunction. A need currently exists to determine a method of treating humans with a hypercoagulable state associated with organ transplantations utilizing activated Protein C.

Burns

It has long been recognized that severely burned patients have complications associated with hypercoagulation [Curreri, et al., *Ann. Surg.* 181:161–163 (1974)]. Burned patients have supranormal in vitro clotting activity and frequently develop DIC which is characterized by the sudden onset of diffuse hemorrhage; the consumption of fibrinogen, platelets, and Factor VIII activity; intravascular hemolysis; secondary fibrinolysis; and biopsy evidence of microthrombi [McManis, et al., *J. of Trauma* 13:416–422, (1973)]. Recently, it was reported that the levels of protein C were reduced drastically in severely burned patients and that this reduction of the natural anticoagulant may lead to an increase in the risk of DIC [Lo, et al., *Burns* 20:186–187 (1994)]. In addition, Ueyama, et al., in discussing the pathogenesis of DIC in the early stage of burn injury, concluded that massive thrombin generation and decrease of anticoagulant activity may occur in proportion to the severity of burns [Ueyama, et al., *Nippon Geka Gakkai Zasshi* 92:907–12 (1991)]. DIC is one of the common complications in patients suffering from severe burn injuries.

Protein C deficiency has been documented in severely burned patients as indicated above, however, there has never been a suggestion to treat patients according to the methods disclosed in the present application.

Pregnancy

It is well known that pregnancy causes multiple changes in the coagulation system which may lead to a hypercoagulable state. For example, during pregnancy and postpartum, the risk of venous thrombosis is almost fivefold higher than in the non-pregnant state. In addition, clotting factors increase, natural inhibitors of coagulation decrease, changes occur in the fibrinolytic system, venous stasis increases, as well as increases in vascular injury at delivery from placental separation, cesarean section, or infection [Barbour, et al., *Obstet Gynecol* 86:621–633, 1995].

Although the risk of a complication due to this hypercoagulable state in women without any risk factors is small, women with a history of thromboembolic events are at an increased risk for recurrence when they become pregnant. In addition, women with underlying hypercoagulable states, including the recent discovery of hereditary resistance to aPC, also have a higher recurrence risk [Dahlback, *Blood* 85:607–614, 1995].

Therefore, it has been suggested that women with a history of venous thromboembolic events who are found to have a deficiency in antithrombin-III, protein C, or protein S, are at an appreciable risk of recurrent thrombosis and should be considered for prophylactic anti-coagulant therapy [Conrad, et al., *Throm Haemost* 63:319–320, 1990]. The conditions of preeclampsia and eclampsia and other obstetrical complications such as amniotic fluid embolism and placenta abruption in pregnant women appear to be a state of increased coagulopathy and disseminated intravascular coagulation as indicated by an increase in fibrin formation, activation of the fibrinolytic system, platelet activation and a decrease in platelet count [*Clin Obstet Gynecol* 35:338–350, 1992]. Preeclampsia is thought to be the result of uteroplacental ischemia due to an anomaly of the "vascular insertion" of the placenta. Consequences of preeclampsia include hypertension as well as DIC which leads to the release of numerous microthrombi which cause placental, renal, hepatic and cerebral lesions [*Rev Fr Gynecol Obstet* 86:158–163, 1991]. Furthermore, preeclampsia can lead to a severe and life threatening condition known as the HELLP syndrome which is defined as preeclampsia complicated by thrombocytopenia, hemolysis and disturbed liver function [Rathgeber, et al., *Anasth Intensivther Notfallmed* 25:206–211, 1990]. Additionally, it has been documented that there is a reduction in protein C levels in pregnant women with severe preeclampsia when compared to normal pregnancies [De Stefano, et al., *Thromb Haemost* 74:793–794, 1995].

Thus, the risk of venous thromboembolic complications occurring in pregnant women is a major concern, especially in women who have a history of thromboembolic events. Although the possibility of severe complications such as preeclampsia or DIC is relatively low, it has been suggested that it is essential to start therapy of DIC as soon as it has been diagnosed by onset of inhibition of the activated coagulation system [Rathgeber, et al., *Anasth Intensivther Notfallmed* 25:206–211, 1990]. The complications of preeclampsia or DIC is analogous to the situation that occurs in sepsis in that there is a hypercoagulable state and a decrease in the levels of protein C (Levi, et al., N. Engl. J. Med. 341:586–592, 1999).

Major Surgery/Trauma

Patients recovering from major surgery or accident trauma frequently encounter blood coagulation complications as a result of an induced hypercoagulable state [Watkins, et al., *Klin Wochenschr* 63:1019–1027, 1985]. Hypercoagulable states are increasingly recognized as causes of venous thromboembolism in surgical patients [Thomas, et al., *Am J Surg*. 158:491–494, 1989; LeClerc, J. R., *Clin Appl Thrombosis/Hemostasis* 3(3):153–156, 1997]. Furthermore, this hypercoagulable state can lead to complications with DIC-like symptoms, which is infrequently encountered but, nonetheless, is devastating and often fatal when it occurs. [Collins, et al., *Am J Surg*. 124:375–380, 1977].

In addition, patients undergoing coronary artery bypass grafting (CABG) [Menges, et al., *J Cardiothor Vasc An*. 10:482–489, 1996], major spinal surgery [Mayer, et al., *Clin Orthop*. 245:83–89, 1989], major abdominal surgery [Blamey, et al., *Thromb Haemost*. 54:622–625, 1985], major orthopedic surgery or arthroplastic surgery of the lower extremities [LeClerc, 1997], or other types of surgery [Thomas, et al., *Am J Surg*. 158:491–494, 1989], occasionally develop venous thromboembolic complications. Additionally, investigators in Japan have proposed treating microvascular thrombosis associated with spinal cord injury [patent application JP8325161A] with plasma derived PCZ at a dose of 1–10 mg/day for an adult, or preferably, 2–6 mg divided by 1–2 times to be administered as a bolus or by intravenous infusion.

It has been suggested that anti-coagulant therapy is important as a prophylactic therapy to prevent venous thromboembolic events in major surgery or trauma patients [Thomas, et al., 1989; LeClerc, 1997]. For example, many patients who succumb from pulmonary embolism have no clinical evidence of preceding thromboembolic events and die before the diagnosis is made and the treatment is instituted [LeClerc, 1997]. Existing prophylactic methods e.g., warfarin, low molecular weight heparins, have limitations such as residual proximal thrombosis or the need for frequent dose adjustments.

Ards

Adult respiratory distress syndrome [ARDS] is characterized by lung edema, microthrombi, inflammatory cell infiltration, and late fibrosis. Pivotal to these multiple cellular and inflammatory responses is the activation of coagulation resulting in a hypercoagulable state. Common ARDS-associated coagulation disorders include intravascular coagulation and inhibition of fibrinolysis. Fibrin formed by the activation of the coagulation system and inhibition of fibrinolysis presumably contributes to the pathogenesis of acute lung injury. Sepsis, trauma and other critical diseases are important risk factors that lead to ARDS [Hasegawa, et al., *Chest* 105(1):268–277, 1994].

ARDS is associated with an activation of coagulation and inhibition of fibrinolysis. Considerable clinical evidence exists for the presence of pulmonary vascular microemboli which is analogous to the hypercoagulation that is present in DIC. Therefore, a need currently exists for an effective treatment of this hypercoagulable state associated with ARDS.

The present invention provides a method of treating human patients with a hypercoagulable state or protein C deficiency which comprises administering to said patient aPC and PCZ.

The invention further provides a method of treating human patients with a hypercoagulable state or protein C deficiency which comprises administering to said patient an effective amount of aPC and PCZ to achieve activated Protein C plasma levels in the range of 2 ng/ml to 200 ng/ml.

Another aspect of this invention provides methods for treating vascular occlusive disorders and acquired and congenital hypercoagulable states, including sepsis (including, severe sepsis and septic shock), disseminated intravascular coagulation, purpura fulminans, major trauma, major surgery, burns, adult respiratory distress syndrome (ARDS), melioidosis, preeclampsia, eclampsia, amniotic fluid embolism, placenta abruption, transplantations, deep vein thrombosis, heparin-induced thrombocytopenia, sickle cell disease, thalassemia, viral hemorrhagic fever, thrombotic thrombocytopenic purpura, hemolytic uremic syndrome, acute coronary syndromes (ACS; e.g., unstable angina, myocardial infarction) and acquired and congenital protein C deficiency, characterized by administering a combination of aPC and PCZ.

Inventive formulations are also provided. Preferably, said formulations are lyophilized, adapted for parenteral administration and comprise aPC and PCZ as the active ingredients in any ratio, together with a pharmaceutical carrier. For example, preferred ratios of PCZ:aPC include: 5% by weight PCZ: 95% by weight aPC; 10% by weight PCZ: 90% by weight aPC; 15% by weight PCZ: 85% by weight aPC; 20% by weight PCZ: 80% by weight aPC; 25% by weight PCZ: 75% by weight aPC; 30% by weight PCZ: 70% by weight aPC; 35% by weight PCZ: 65% by weight aPC; 40% by weight PCZ: 60% by weight aPC; 45% by weight PCZ: 55% by weight aPC; and 50% by weight PCZ: 50% by weight aPC; 60% by weight PCZ: 40% by weight aPC; 70% by weight PCZ: 30% by weight aPC; 80% by weight PCZ: 20% by weight aPC; 90% by weight PCZ: 10% by weight aPC; 95% by weight PCZ: 5% by weight aPC; 99% by weight PCZ: 1% by weight aPC. Preferably, said formulations further comprise a salt (e.g., sodium chloride, calcium chloride, potassium chloride), a bulking agent (e.g., mannitol, trehalose, raffinose, sucrose, or mixtures of various bulking agents), a buffer (e.g., Tris-acetate, sodium citrate, and sodium phosphate, or mixtures of buffers), and optionally, a stabilizer (e.g., albumin). The formulations herein, upon reconstitution with an acceptable diluent, have preferred pH ranges and values, as follows: pH of about 6.0 to about 8.0; pH of about 6.0 to about 7.0; pH of about 6.3 to about 6.7. The inventive formulations are preferably adapted for use in treating the methods described herein. The formulations may be prepared via multiple methods, including by lyophilizing a solution comprising aPC, PCZ, and a bulking agent. Preferably, the solution to be lyophilized further comprises a salt and/or a buffer, and optionally a stabilizing agent. Also included, is an article of manufacture, comprising packaging material and activated Protein C contained within said packaging material, wherein the packaging material comprises a label which indicates that activated Protein C can be used in combination with protein C zymogen for treating a disease or condition selected from: sepsis, severe sepsis, septic shock, disseminated intravascular coagulation, purpura fulminans, major trauma, undergoing or recovering from surgery, burns, adult respiratory distress syndrome, bone marrow and other organ transplantations, deep vein thrombosis, heparin-induced thrombocytopenia, sickle cell disease, thalassemia, viral hemorrhagic fever, thrombotic thrombocytopenic purpura, hemolytic uremic syndrome, unstable angina, myocardial infarction, meningococcemia, melioidosis, complications during pregnancy, preeclampsia, eclampsia, amniotic fluid embolism, placental abruption, and chemotherapy.

For purposes of the present invention, as disclosed and claimed herein, the following terms are as defined below.

APC, aPC, or activated Protein C refer to the activated human protein C molecule, whether plasma derived or produced by recombinant or transgenic means. Recombinant and transgenic activated Protein C may be produced by activating the human protein C zymogen in vitro or by direct secretion or production of the activated form of protein C. Protein C may be produced in cells, eukaryotic cells, transgenic animals, or transgenic plants, including, for example, secretion from human kidney 293 cells as a zymogen then purified and activated by techniques known to the skilled artisan.

Treating—describes the management and care of a patient for the purpose of combating a disease, condition, or disorder. Treating may also include prophylaxis, preventing or prophylactic administration to prevent the onset of the symptoms or complications of the disease, condition, or disorder.

Continuous infusion—continuing substantially uninterrupted the introduction of a solution into a vein for a specified period of time.

Bolus injection—the injection of a drug in a defined quantity (called a bolus) over a period of time, for example, up to about 1–120 minutes.

Suitable for administration—a formulation or solution that is appropriate to be given as a therapeutic agent.

Receptacle—a container such as a vial or bottle that is used to receive the designated material, i.e., PCZ or aPC or combinations thereof.

Unit dosage form—refers to physically discrete units suitable as unitary dosages for human subjects, each unit containing a predetermined quantity of active material calculated to produce the desired therapeutic effect, in association with a suitable pharmaceutical excipient.

Hypercoagulable states—excessive coagulability associated with disseminated intravascular coagulation, prethrombotic conditions, activation of coagulation, or congenital or acquired deficiency of clotting factors such as PCZ.

Zymogen—Protein C zymogen, as used herein, refers to secreted, inactive forms, whether one chain or two chains, of protein C.

Juvenile—a human patient including but not restricted to newborns, infants, and children younger than 18 years of age.

Effective amount—a therapeutically efficacious amount of a pharmaceutical compound or compounds, particularly aPC and/or PCZ.

Purpura fulminans—ecchymotic skin lesions, fever, hypotension associated with bacterial sepsis, viral, bacterial or protozoan infections. Disseminated intravascular coagulation is usually present.

Sepsis-refers to a systemic response to infection or suspected infection complicated by one or more organ failures. For purposes of this application, the term "sepsis" also includes severe sepsis (sepsis with evidence of one of more organ failure. Organs can be cardiovascular, metabolic, mental status/central nervous system, hematologic/coagulation, renal, respiratory, hepatic) and septic shock (defined as hypotension or hypoperfusion to end organs).

Protein C deficiency can be determined and defined by two primary means depending upon the availability of patient data. For a patient whose normal plasma protein C level is known, or if serial plasma protein C level is performed on a patient (for example, every 6–12 hours), acquired protein C deficiency can be defined as a 10% or greater decrease from either the patient's own known normal level or from a recent protein C level value that was within a normal range. When a patient's normal plasma protein C level is not known or cannot be obtained (for example, a patient upon admission to the hospital is already presenting with clinical symptoms of severe sepsis or laboratory tests indicate a hypercoagulable state), then the acquired protein C deficiency is generally defined as below the lower limit of the normal range of protein C as established or used by the laboratory that performs the protein C assay.

The present invention relates to the treatment or prevention of hypercoagulable states or acquired protein C deficiency, particularly when such states or deficiency is associated with: sepsis, transplantation, burns, pregnancy, major surgery, trauma, or ARDS, with aPC and PCZ. The aPC and PCZ can be made by techniques well known in the art utilizing eukaryotic cell lines, transgenic animals, or transgenic plants. Skilled artisans will readily understand that appropriate host eukaryotic cell lines include but are not limited to HEPG-2, LLC-MK$_2$, CHO-K1, 293, or AV12 cells, examples of which are described by Grinnell in U.S. Pat. No. 5,681,932, herein incorporated by reference. Furthermore, examples of transgenic production of recombinant proteins are described by Drohan, et al., in U.S. Patent No. 5,589,604 and Archibald, et al., U.S. Patent No. 5,650,503, herein incorporated by reference. U.S. Patent No. 5,009,889 (incorporated by reference herein) describes various procedures for isolating protein C from plasma. For additional examples of methods to prepare PCZ and aPC, and formulations containing the same, See: U.S. Pat. 5,580,962 (columns 3 and 4); U.S. Pat. 5,831,025; European Patent Application 0662513A1; U.S. Pat. No. 5,093,117; and U.S. Pat. No. 5,084,273.

To be fully active, the aPC made by any of these methods must undergo post-translational modifications such as the carboxylation of the side-chain of nine glutamate residues to gamma-carboxy-glutamates (gamma-carboxylation, i.e., Gla content), the hydroxylation of the side chain of one aspartate residue to erythro-beta-hydroxy-Asp (beta-hydroxylation), the glycosylation of the side chain of four asparagine residues to Asn-linked oligosaccharides (glycosylation), the removal of the leader sequence (42 amino acid residues) and removal of the dipeptide Lys 156-Arg 157. Without such post-translational modifications, aPC is not fully functional or is non-functional.

The following Methods, Preparations and Examples are illustrative and are not intended to limit the invention in any way.

Method for Determining Protein C Levels in Patient Plasma Samples

Protein C levels can be determined in patient citrated plasma samples using appropriately approved diagnostic kits by appropriately certified laboratories and trained laboratory technicians. There are generally three types of diagnostic kits for measuring protein C levels from various commercial companies. One is to measure the antigenic level of protein C in plasma by an ELISA type methodology. The other two methods are to measure the protein C activity level. Protein C is first converted to activated Protein C, generally using a protease extracted from snake venom, and then the activity is measured either by its amidolytic activity (amidolytic activity kit) or by its anticoagulant activity (clotting activity kit). Any of the three diagnostic kits can be used to determine protein C deficiency in patients. For acquired protein C deficiency or an acquired hypercoagulable state where liver dysfunction may be involved, the preferred or more clinically relevant method for determining the protein C level in a patient is the clotting activity diagnostic kit.

Protein C levels are usually measured in patient citrated plasma. A patient's blood sample is usually collected into either a 2.8 ml (pediatric size) or 4.5 ml vacutainer containing either 3.2% or 3.8% citrate. The blood sample can be obtained either via veni-puncture or via a central line. If heparin contamination cannot be avoided when collecting the blood sample, for example, via central line, then only the antigenic method can be used to measure accurately the protein C levels in that sample. The citrated blood sample is centrifuged at about 2000×g for 10 to 20 minutes. The citrated plasma, which is the supernatant can be removed and used for the protein C level measurement.

The measurement of plasma protein C levels using any one of the three kinds of diagnostic kits can be carried out using manual, semi-automated or automated equipment. Appropriately certified laboratories and technicians usually have detailed standard operating procedures for performing the protein C assays. The standard operating procedures should include appropriate validation of the assays and the equipment used prior to assaying patient samples. In general, human plasma standard samples with known levels of protein C are used to calibrate and validate the assay and equipment. The intra- and inter-day variation of the assay results using these known standards should be less than 10% CV.

Determination of Normal (100%) Level of Human Plasma Protein C

Normal (100%) of human plasma protein C level is defined as the amount of protein C in a pooled normal plasma sample. This pooled normal human plasma sample can be the established WHO international standard (1 ml of pooled citrated plasma). This can also be supplied as part of the commercially available protein C diagnostic kit. This is usually prepared by combining citrated plasma from 20 to more than a hundred normal human donors. The pooled plasma is then aliquoted and generally stored as a 1 ml lyophilized or frozen liquid in vials with specified expiration date.

Determination of Normal Range of Human Plasma Protein C

The normal range of human plasma protein C is generally determined by each laboratory as part of the validation for determining human plasma protein C level for the purpose of providing clinical diagnosis of the patient by the clinical staff. The normal range will vary slightly from laboratory to laboratory depending upon the diagnostic kit/method and the equipment used to perform the protein C assay. A concentration standard curve is determined with the standards provided and the procedure accompanied by the diagnostic kit and the equipment. The normal range is determined by measuring the concentration of protein C in a citrated plasma sample from about 30–120 normal healthy individual donors who are not on any medications that can affect their blood clotting chemistry. The lower and upper limit of the normal range are determined by taking two standard deviations from the mean (if the range is of normal distribution) or the median (if the range is not of normal distribution). The lower limit of normal range for adult human ($\geq$18 years of age) is usually around 60–80% of pooled normal plasma. The upper limit of normal range for adult human ($\geq$18 years of age) is usually around 140–180%. A normal new born usually has a plasma protein C level of about 30–40% of an normal adult. By about 1 year of age, the plasma protein C level in a normal child will reach to about the lower limit of a normal adult. Thus the normal range in children is different from that of adult and needs to be determined separately.

Preparation 1

Preparation of Human PCZ

Recombinant human PCZ was produced in Human Kidney 293 cells by techniques well known to the skilled artisan such as those set forth in Yan, U.S. Pat. No. 4,981,952, the entire teaching of which is herein incorporated by reference. The gene encoding human protein C is disclosed and claimed in Bang, et al., U.S. Pat. No. 4,775,624, the entire teaching of which is incorporated herein by reference. The plasmid used to express human protein C in 293 cells was plasmid PLPC which is disclosed in Bang, et al., U.S. Pat. No. 4,992,373, the entire teaching of which is incorporated herein by reference. The construction of plasmid pLPC is also described in European Patent Publication No. 0 445 939, and in Grinnell, et al., 1987, *Bio/Technology* 5:1189–1192, the teachings of which are also incorporated herein by reference. Briefly, the plasmid was transfected into 293 cells, then stable transformants were identified, subcultured and grown in serum-free media. After fermentation, cell-free medium was obtained by microfiltration.

The human protein C was separated from the culture fluid by an adaptation of the techniques of Yan, U.S. Pat. No. 4,981,952, the entire teaching of which is herein incorporated by reference. The clarified medium was made 4 mM in EDTA before it was absorbed to an anion exchange resin (Fast-Flow Q, Pharmacia). After washing with 4 column volumes of 20 mM Tris, 200 mM NaCl, pH 7.4 and 2 column volumes of 20 mM Tris, 150 mM NaCl, pH 7.4, the bound recombinant human PCZ was eluted with 20 mM Tris, 150 mM NaCl, 10 mM $CaCl_2$, pH 7.4. The eluted protein was greater than 95% pure after elution as judged by SDS-polyacrylamide gel electrophoresis.

Further purification of the protein was accomplished by making the protein 3 M in NaCl followed by adsorption to a hydrophobic interaction resin (Toyopearl Phenyl 650 M, TosoHaas) equilibrated in 20 mM Tris, 3 M NaCl, 10 mM $CaCl_2$, pH 7.4. After washing with 2 column volumes of equilibration buffer without $CaCl_2$, the recombinant human protein C was eluted with 20 mM Tris, pH 7.4.

The eluted protein was prepared for activation by removal of residual calcium. The recombinant human protein C was passed over a metal affinity column (Chelex-100, Bio-Rad) to remove calcium and again bound to an anion exchanger (Fast Flow Q, Pharmacia). Both of these columns were arranged in series and equilibrated in 20 mM Tris, 150 mM NaCl, 5 mM EDTA, pH 6.5. Following loading of the protein, the Chelex-100 column was washed with one column volume of the same buffer before disconnecting it from the series. The anion exchange column was washed with 3 column volumes of equilibration buffer before eluting the protein with 400 mM NaCl, 20 mM Tris-acetate, pH 6.5. Protein concentrations of recombinant human PCZ and recombinant aPC solutions were measured by UV 280 nm extinction $E^{0.1\%}$=1.85 or 1.95, respectively.

Preparation 2

Activation of Recombinant Human PCZ

Bovine thrombin was coupled to Activated CH-Sepharose 4B (Pharmacia) in the presence of 50 mM HEPES, pH 7.5 at 4° C. The coupling reaction was done on resin already packed into a column using approximately 5000 units thrombin/ml resin. The thrombin solution was circulated through the column for approximately 3 hours before adding MEA to a concentration of 0.6 ml/l of circulating solution. The MEA-containing solution was circulated for an additional 10–12 hours to assure complete blockage of the unreacted amines on the resin. Following blocking, the thrombin-coupled resin was washed with 10 column volumes of 1 M NaCl, 20 mM Tris, pH 6.5 to remove all non-specifically bound protein, and was used in activation reactions after equilibrating in activation buffer.

Purified PCZ was made 5 mM in EDTA (to chelate any residual calcium) and diluted to a concentration of 2 mg/ml with 20 mM Tris, pH 7.4 or 20 mM Tris-acetate, pH 6.5. This material was passed through a thrombin column equilibrated at 37° C. with 50 mM NaCl and either 20 mM Tris pH 7.4 or 20 mM Tris-acetate pH 6.5. The flow rate was adjusted to allow for approximately 20 min. of contact time between the PCZ and thrombin resin. The effluent was collected and immediately assayed for amidolytic activity. If the material did not have a specific activity (amidolytic) comparable to an established standard of aPC, it was recycled over the thrombin column to activate the PCZ to completion. This was followed by 1:1 dilution of the material with 20 mM buffer as above, with a pH of anywhere between 7.4 or 6.0 (lower pH being preferable to prevent autodegradation) to keep the aPC at lower concentrations while it awaited the next processing step.

Removal of leached thrombin from the aPC material was accomplished by binding the aPC to an anion exchange resin (Fast Flow Q, Pharmacia) equilibrated in activation buffer (either 20 mM Tris, pH 7.4 or preferably 20 mM Tris-acetate, pH 6.5) with 150 mm NaCl. Thrombin passes through the column and elutes during a 2–6 column volume wash with 20 mM equilibration buffer. Bound aPC is eluted with a step gradient using 400 mM NaCl in either 5 mM Tris-acetate, pH 6.5 or 20 mM Tris, pH 7.4. Higher volume washes of the column facilitated more complete removal of the dodecapeptide. The material eluted from this column was stored either in a frozen solution (−20° C.) or as a lyophilized powder.

The amidolytic activity (AU) of aPC was determined by release of p-nitroanaline from the synthetic substrate H-D-Phe-Pip-Arg-p-nitroanilide (S-2238) purchased from Kabi Vitrum using a Beckman DU-7400 diode array spectrophotometer. One unit of aPC was defined as the amount of enzyme required for the release of 1 µmol of p-nitroaniline in 1 min. at 25° C., pH 7.4, using an extinction coefficient for p-nitroaniline at 405 nm of 9620 $M^{-1}$ $cm^{-1}$.

The anticoagulant activity of aPC was determined by measuring the prolongation of the clotting time in the activated partial thromboplastin time (APTT) clotting assay. A standard curve was prepared in dilution buffer (1 mg/ml radioimmunoassay grade BSA, 20 mM Tris, pH 7.4, 150 mM NaCl, 0.02% $NaN_3$) ranging in protein C concentration from 125–1000 ng/ml, while samples were prepared at several dilutions in this concentration range. To each sample cuvette, 50 µl of cold horse plasma and 50 µl of reconstituted activated partial thromboplastin time reagent (APTT Reagent, Sigma) were added and incubated at 37° C. for 5 min. After incubation, 50 µl of the appropriate samples or standards were added to each cuvette. Dilution buffer was used in place of sample or standard to determine basal clotting time. The timer of the fibrometer (CoA Screener Hemostasis Analyzer, American Labor) was started upon the addition of 50 µl, 37° C., and 30 mM $CaCl_2$ to each sample or standard. aPC concentration in samples is calculated from the linear regression equation of the standard curve. Clotting times reported here are the average of a minimum of three replicates, including standard curve samples.

The above descriptions enable one with appropriate skill in the art to prepare PCZ and aPC for use in treating the hypercoagulable states or acquired protein C deficiency as described herein.

EXAMPLE 1

Human Plasma Levels of aPC

Six human patients received an intravenous infusion of aPC at 1 $mg/m^2/hr$ or about 0.024 mg/kg/hr over a 24 hour period. The aPC administered was a lyophilized formulation containing 10 mg aPC, 5 mM Tris acetate buffer and 100 mM sodium chloride reconstituted with two ml of water and adjusted to pH 6.5.

Plasma concentrations of aPC were measured using an Immunocapture-Amidolytic Assay. Blood was collected in the presence of citrate anticoagulant and benzamidine, a reversible inhibitor of aPC. The enzyme was captured from plasma by an aPC specific murine monoclonal antibody, C3, immobilized on a microtiter plate. The inhibitor was removed by washing and the amidolytic activity of aPC was measured using an oligopeptide chromogenic substrate. Following incubation for 16–20 hours at 37° C., the absorbance was measured at 405 nm and data are analyzed by a weighted linear curve-fitting algorithm. aPC concentrations were estimated from a standard curve ranging in concentrations from 0–100 ng/ml. The limit of quantitation of the assay was 1.0 ng/ml. The aPC dose levels and plasma concentrations were measured at about 24 hours. The dose of 0.024 mg/kg/hr yields a plasma concentration of about 50 ng/ml at 24 hours.

EXAMPLE 2

Double-blinded Placebo-controlled Trial in Human Patients With Sepsis, Stage 1

This protocol is a two-stage, double-blinded placebo-controlled trial in patients with severe sepsis. In Stage 1, a total of 72 patients were infused for 48 hours with recombinant human aPC.

Entry criteria included three of the four commonly accepted criteria for sepsis (heart rate, respiratory effort, increased/decreased temperature, increase/decrease white blood cell count). The patients also had to demonstrate some degree of organ dysfunction defined as either shock, decreased urine output, or hypoxemia. Four different doses were utilized; 12, 18, 24, 30 µg/kg/hr. The aPC was infused for 48 hours by a continuous infusion method. The primary endpoints of this study were: safety as a function of dose and dose duration, and the ability of aPC to correct coagulopathy as a function of dose and dose duration.

Mortality information includes all doses, even the lowest doses, unless otherwise specified. It is important to note that the placebo mortality observed in this study is consistent with anticipated placebo mortality. A 28 day all cause mortality was the end-point in patients receiving placebo vs. patients receiving aPC.

The overall observed placebo mortality rate was 38% (10/26) and the overall observed aPC mortality rate was 20% (9/46). A subgroup involving only the top two doses of aPC (24 and 30 µg/kg/hr) vs. placebo patients had an observed mortality rate of 13% (3/24).

A second subgroup analysis included patients with an acquired protein C deficiency, defined as a baseline protein C activity of less than 60%. Of the 64 patients that have baseline protein C activity data available, 61 patients or 95%, had an acquired protein C deficiency at the time of entry into the study. The observed placebo mortality rate for protein C deficient patients was 41% (9/22) and the observed aPC mortality rate for protein C deficient patients was 18% (7/39).

A significant piece of information suggesting that treatment with aPC is of benefit with patients with severe sepsis includes the mean time to death in placebo patients vs. treated patients. Of the 10 patients who died in the placebo group, the mean time to death was 6 days. In the aPC treated patients, the mean time to death was 14 days. Additionally, 4 of the 9 patients who died in the aPC treatment arm survived 21 or more days and subsequently succumbed to an event unrelated to their first episode of sepsis. Two of the four late deaths occurred in the low dose group (12 µg/kg/hr). Both of these patients remained in the ICU and mechanically ventilated the entire duration of the study until their death (day 27). The other two patients with late deaths were in the higher dose group (30 µg/kg/hr). Both of these patients showed initial improvement. Within two weeks both were off mechanical ventilation and transferred from the ICU. One patient died a week later from sepsis induced respiratory distress after requesting a "do not resuscitate" (DNR) order enacted. The second patient died on day 28 after suffering an episode of pulmonary insufficiency related to a second episode of sepsis. This patient had also requested DNR status and therefore was not reintubated. It should be noted that retreatment with aPC of patients that develop a second episode of severe sepsis during the 28 day study was not approved under the treatment protocol.

The mortality information in this study is surprising and unexpected. No other double-blinded, placebo controlled sepsis study has generated data demonstrating such a marked reduction in 28 day all cause mortality.

The administration of PCZ and aPC in order to practice the present methods of therapy is carried out by administering an effective amount of each chosen compound (PCZ and/or aPC) to the patient in need thereof. The effective amount of each individual compound, and the appropriate dosing regimen, is determined, in the final analysis, by the physician in charge of the case, but depends on factors such as the exact disease or diseases to be treated, the severity of the disease and other diseases or conditions from which the patient suffers, the specific route of administration, other drugs and treatments which the patient may concomitantly require, and no doubt other factors in the physician's judgement.

Preferably the aPC is administered by continuous infusion for about 24 to about 144 hours at a dosage of about 1 µg/kg/hr to about 50 µg/kg/hr. More preferably, the amount of aPC administered will be about 4 µg/kg/hr to about 48 µg/kg/hr. Even more preferably the amount of aPC administered will be: about 6 µg/kg/hr to about 44 µg/kg/hr; about 8 µg/kg/hr to about 40 µg/kg/hr; about 10 µg/kg/hr to about 36 µg/kg/hr; about 12 µg/kg/hr to about 34 µg/kg/hr; about 14 µg/kg/hr to about 30 µg/kg/hr; about 16 µg/kg/hr to about 24 µg/kg/hr; about 18 µg/kg/hr to about 20 µg/kg/hr; about 6 µg/kg/hr to about 22 µg/kg/hr; or about 10 µg/kg/hr to about 20 µg/kg/hr; or about 5 µg/kg/hr to about 25 µg/kg/hr; or about 5 µg/kg/hr to about 30 µg/kg/hr. The preferred amounts of PCZ administered will be about 4 µg/kg/hr to about 800 µg/kg/hr; about 20 µg/kg/hr to about 600 µg/kg/hr; 40 µg/kg/hr to about 400 µg/kg/hr; 60 µg/kg/hr to about 120 µg/kg/hr; 80 µg/kg/hr to about 200 µg/kg/hr; or 100 µg/kg/hr to about 150 µg/kg/hr; or about 25 µg g/kg/hr to 100 µg/kg/hr (infusion only), more preferably about 40 µg/kg/hr to about 80 µg/kg/hr (infusion); and most preferably about 90 µg/kg/hr, infusion only. Alternatively, a bolus may be administered at various intervals before during or after discontinuation of the infusion. The bolus is preferably in the range of about or about 25 to 100 µg/kg/hr to about 500 µg/kg/hr (bolus followed by infusion); or about 200 µg/kg to 2000 µg/kg once daily.

A physician may dose the PCZ and aPC to achieve preferred PCZ and/or aPC plasma levels. Should the physician desire rapid aPC plasma levels, aPC will be administered in a bolus or in an increased amount. aPC will also be preferred when it appears that a patient is not responding to PCZ, possibly because of a perceived or documented inability of a patient to convert PCZ to aPC. Examples of preferred protein C plasma level-ranges include: about 10 ng/ml to about 180 ng/ml; about 25 ng/ml to about 160 ng/ml; about 25 ng/ml to about 100 ng/ml; about 30 ng/ml to about 140 ng/ml; about 40 ng/ml to about 120 ng/ml; about 40 ng/ml to about 100 ng/ml; and about 40 to about 80 ng/ml. Again, although the preferred doses and plasma ranges are stated herein, various boluses of PCZ and/or aPC may be used at various intervals, as is preferred in the judgement of the physician.

For examples of dosing regimens of aPC and PCZ noted in literature and patent documents, Table I sets forth normalized dose levels of several studies in humans or non-human primates. The human studies were done utilizing plasma derived PCZ while the non-human primate study utilized recombinant human aPC.

TABLE I

| REFERENCE | PUBLISHED DOSE | NORMALIZED DOSE+ |
| --- | --- | --- |
| Taylor, et al., U.S. Pat. No. 5,009,889 | IV administration of between 2 and 64 µg aPC/kg/minute; a bolus of between 1 and 10 mg aPC may be given additionally. [column 5, lines 14–19] | 120 µ/kg/hr to 3800 ug/kg/hr infused for 8 to 10 hours |
| Rivard, et al., J. Ped. 126: 646, 1995 | IV administration at a dose of 100 IU*/kg plasma derived protein C zymogen during a 15 to 20 minute period every 6 hours during the acute phase and then 1 to 2 times a day for 9 days. [p.648, column 1, 1st paragraph] | 400 ug/kg in 15 to 20 minutes |
| Gerson, et al., Ped. 91: 418–422, 1993 | IV administration at a bolus dose of 70 IU*/kg plasma derived protein C zymogen every 6 hours. Subsequently, continuous infusion of 10 IU/kg/hr for 11 days was given. [p.419, column 2, 1st paragraph] | 280 ug/kg bolus every 6 hours, then continuous infusion of 40 ug/kg/hr for 11 days |
| Rintala, et al., Lancet 347: 1767, 1996 | IV administration was started 3 hours after admission and continued for 7 days. 100 IU*/kg plasma derived protein C zymogen every 6 hours and later adjusting dose to plasma protein C activity. [p.1767, column 2, 2nd paragraph] | 400 ug/kg bolus every 6 to 8 hours for 7 days |
| Ettingshausen, et al., Semin. Thromb. Hemost. 25: 537–541, 1999 | Plasma-derived human protein C treatment was initiated on the day of admission and continued for 1 to 16 days. Each patient received an initial bolus of 80 to 120 IU*/kg or protein C followed by a one hour infusion of 50 IU*/kg protein C, given once every 4 hours during the early acute phase of the illness. The frequency of the hourly infusion was adjusted with once or twice daily monitoring of the endogenous protein C level to aim at maintaining an endogenous protein C level in the normal range. [p.538, column 2, 2nd paragraph] | 320 to 480 µg/kg bolus + 50 µg/kg/hr infusion for 3 days (median) with a range of 1 to 16 days. |
| Betrosian, et al. Crit. Care Med. 27: 2849–2850, 1999 | Plasma-derived human protein C treatment was initiated 48 hours after admission and continued for 3 days. The patient was given 100 IU*/kg by IV administration once every 6 hours the first day and at 60 IU*/kg every 6 hours the subsequent 2 days. The endogenous protein C level was maintained at 85 to 140% during the therapy. [p.2850, column 1, 1st paragraph] | 67 µg/kg/hr was given the first 24 hours and 40 µg/kg/hr was given the 2 additional days. |
| Veldman et al., Bone Marrow Transplant. 21: S238, 1998 | Plasma-derived human protein C treatment was initiated the same time as heparin and t–PA treatment for 18 days. Protein C was given as intravenous infusion of 60 IU*/kg/24 hours. [p.S238, column 2, abstract # 834] | 10 µg/kg/hr for 18 days |
| Toupance et al., Transpl. Int. 7: 144–145, 1994 | Plasma-derived human protein C was given prophylactically before and after renal transplant at 50 IU*/kg twice daily for 10 days and once daily for 7 more days. During the next 6 months after renal transplant, protein C was given as treatment for several thrombotic crisis at the same dose for about 10 days each time. [p.145, column 1, 2nd paragraph) | 4 to 8 µg/kg/hr for 10 to 17 days in a prophylactic and treatment modes |
| Favier, et al., Hematol. Cell Therapy 40: 67–70, 1998 | Plasma-derived human protein C treatment was initiated 6 days after admission and was given intravenously at 10 IU*/kg/10 hours for 6 days. The treatment was stopped for 4 days and resumed for 5 days. [p.69, column 1, 1st and 2nd paragraphs] | 4 µg/kg/hr for 6 days, stopped for 4 days and treated again at the same dose for 5 days |
| Minford, et al., Br. J. Haematol. 93: 215–216, 1996 | Plasma-derived human protein C treatment was given by subcutaneous infusion over 2 hours via a Graseby syringe pump at 250 IU*/kg every 48 hours for long term therapy. This raised the protein C level in the patient at a peak of about 90% to a nadir of about 25% in between dosing. [p.215, column 2, 1st paragraph] | 1000 µg/kg subcutaneous every 48 hours for long term therapy |
| San–Rodriguez, et al., Br. J. Haematol. 102: 16, 1998 | Plasma-derived human protein C treatment was given by subcutaneous route at 350 IU*/kg every 48 hours for 9 months and beyond for long term therapy. [p.16, column 2, #0–0059] | 1400 µg/kg subcutaneous every 48 hours for long term therapy |
| Smith, et al., Lancet, 350: 1590–1593, 1997 | Plasma-derived human protein C treatment was initiated 8 to 72 hours after admission and continued for 1 to 8 days. Each patient had a test dose of 40 IU*/kg over 10 min. Then a loading dose of 100 IU*/kg plasma derived protein C zymogen followed by a continuous | 400 ug/kg bolus + 60 ug/kg/hr for 5.7 days (mean) with a range of 1 to 8 days |

TABLE I-continued

| REFERENCE | PUBLISHED DOSE | NORMALIZED DOSE+ |
|---|---|---|
| | infusion of 15* IU/kg. [p.1591, column 2, 4$^{th}$ paragraph] | |
| Fujiwara, et al., Japanese Patent JP7097335A | The usual dose is 20–1000 U** plasma derived APC/kg body weight/day, or more preferably 50–300 U/kg with divided administration of 1–2 times. As the method of administration, it is most appropriate to use intravenous infusion. [p.9, paragraph 0016] | 4 ug/kg to 200 ug/kg. An infusion time was not given. |
| Okajima, et al., Japanese Patent JP 8325161A | The effective dose of plasma derived PC or APC is 1–10 mg/day for an adult, or preferably 2–6 mg to be administered divided 1–2 times. As the method of administration, one can use bolus administration (in a single administration) or intravenous infusion. [p.10, paragraph 0013] | 42 ug/hr to 420 ug/hr |
| Okajima, et al., Amer. J of Hematology, 33: 277–278 (1990) | Administration of plasma derived aPC (3 †mg/day for 2 days, followed by 6 mg/day for 3 days). [p.278, column 1, 1$^{st}$ full paragraph] | 2 ug/kg/hr and 4 ug/kg/hr. |
| Kobayashi, et al., Thromb. Haemost. 82: 1363, 1999 | Plasma-derived human aPC was given at 5000 to 10000 units** over 2 days. [p.1363, column 1, 2$^{nd}$ paragraph] | 21 to 42 µg/hr for 2 days |
| Wada, et al., Am. J. Hematol. 44: 218–219, 1993 | Plasma-derived human APC was given at 4000 units**/day for 6 days. [p.219, column 1, 1$^{st}$ paragraph] | 33 µg/hr for 6 days |
| Wada, et al., Blood 94: 28a, 1999 | Plasma-derived human APC was given at 100 to 300 units**/kg for 3 to 6 days. This dose is not sufficient for treating purpura fulminans. [p.28a, column 2, #111] | 0.8 to 2.5 µg/kg/hr for 3 to 6 days |
| Bang, et al., U.S. Pat. No. 4,775,624 | The dose of activated Protein C ranges from 1–10 mg as a loading dose followed by a continuous infusion in amounts ranging from 3–30 mg/day. [column 19, lines 55–59] | 1.8 to 18 ug/kg/hr An infusion time was not given. |

*the normalized dose is a conversion of the reported dose to the equivalent ug/kg/hr designation.
•1 IU is equivalent to approximately 4 ug of PC
**1 U is defined as the amount which doubles the activated prothrombin time (APTT) in normal human plasma. This converts to approximately 5 Units/ug APC.

Another embodiment of the present invention is a pharmaceutical formulation comprising an effective amount of aPC and PCZ. The aPC and PCZ can be formulated together in a formulation according to known methods to prepare pharmaceutically useful compositions. Preferably the aPC and PCZ formulation will comprise, consist essentially of, or consist of, a salt; such as, sodium, or calcium or potassium chloride, a bulking agent, preferably sucrose, mannitol, dextran, trehalose, or raffinose; and a buffer, preferably a phosphate or sodium chloride buffer, and most preferably a buffer selected from Tris-acetate, sodium citrate, sodium phosphate and combinations thereof. A stabilizer, such as albumin, may also be added. To prevent or reduce the autodegration of PCZ and aPC, purification and/or formulation may be performed in the presence of a denaturing agent. For example, urea may be used at concentrations of about 3 M. The formulation is preferably a lyophilized formulation. The active ingredients may be in any ratio, for example, preferred ratios of PCZ: aPC include: 5% by weight PCZ: 95% by weight aPC; 10% by weight PCZ: 90% by weight aPC; 15% by weight PCZ: 85% by weight aPC; 20% by weight PCZ: 80% by weight aPC; 25% by weight PCZ: 75% by weight aPC; 30% by weight PCZ: 70% by weight aPC; 35% by weight PCZ: 65% by weight aPC; 40% by weight PCZ: 60% by weight aPC; 45% by weight PCZ: 55% by weight aPC; and 50% by weight PCZ: 50% by weight aPC; 60% by weight PCZ: 50% by weight aPC; 70% by weight PCZ: 30% by weight aPC; 80% by weight PCZ: 20% by weight aPC; 90% by weight PCZ: 10% by weight aPC; 95% by weight PCZ: 5% by weight aPC; 99% by weight PCZ: 1% by weight aPC.

The present formulations are prepared by known procedures using well-known and readily available ingredients. Preferably, the PCZ and aPC will be administered parenterally to ensure delivery into the bloodstream in an effective form. Preferably, aPC and PCZ may be formulated according to the disclosure herein. The aPC/PCZ fixed mixtures provide various advantages, including cost savings and administering convenience and compliance. A vial or other dosage receptacle of either aPC or PCZ will not have to be opened to obtain a small quantity of the active ingredient, thus allowing the remainder of the active ingredient to become unstable or unusable. The fixed mixtures will also save time by eliminating mixing and/or multiple dosing. Mixing errors should also be reduced.

EXAMPLE 3

Formulation of APC/PCZ

A stable lyophilized formulation of aPC is prepared by a process which comprises lyophilizing a solution comprising about 2.5 mg/mL aPC or PCZ, about 15 mg/mL sucrose, about 20 mg/mL NaCl, and a sodium citrate buffer having a pH greater than 5.5 but less than 6.5. Additionally, the stable lyophilized formulation of aPC and PCZ comprises lyophilizing a solution comprising about 5 mg/mL aPC and PCZ, about 30 mg/mL sucrose, about 38 mg/mL NaCl, and a citrate buffer having a pH greater than 5.5 and, preferably, less than 6.5.

The ratio of aPC/PCZ:salt:bulking agent (w:w:w) is believed to be an important factor in a formulation suitable for the freeze drying process. The ratio varies depending on the concentration of aPC/PCZ, salt selection and concentration and bulking agent selection and concentration. Particularly, a ratio of about 1 part aPC/PCZ to about 7.6 parts salt to about 6 parts bulking agent is believed to be preferred.

A unit dosage formulation of aPC/PCZ suitable for parenteral administration, preferably subcutaneous administration or continuous intravenous infusion is prepared by mixing aPC, PCZ, NaCl, sucrose, and sodium citrate buffer. After mixing, 4 mL of the solution is transferred to a unit dosage receptacle and lyophilized. The unit dosage receptacle containing about 5 mg to about 20 mg of aPC/PCZ, suitable for administering a dosage of about 0.02 mg/kg/hr to about 0.05 mg/kg/hr to patients in need thereof, is sealed and stored until use.

EXAMPLE 4 aPC/PCZ Formulations

A unit dosage formulation of aPC and PCZ suitable for parenteral administration is prepared by mixing 0.5 mg of aPC, 1.0 mg of PCZ, 90 mg of NaCl, 100 mg of mannitol, 50 USP units of heparin, 22.5 mg of aminoacetic acid, and 25 mg of human serum albumin. After mixing, 10 mL of the solution is transferred to a unit dosage receptacle and lyophilized. The unit dosage is sealed.

EXAMPLE 5 aPC/PCZ Formulations

A unit dosage formulation of aPC and PCZ suitable for parenteral administration administration or continuous infusion is prepared by mixing 1.0 mg of aPC, 1.0 mg of PCZ, 90 mg of NaCl, 100 mg of mannitol, 50 USP units of heparin, 22.5 mg of aminoacetic acid, and 25 mg of human serum albumin. After mixing, 10 mL of the solution is transferred to a unit dosage receptacle and lyophilized. The unit dosage is sealed. The same experiment may be repeated where the ratio of aPC: PCZ varies from 1 to 99% by weight aPC to 1 to 99% PCZ.

EXAMPLE 6 aPC/PCZ Formulations

A stable lyophilized formulation of aPC/PCZ may be prepared by a process which comprises lyophilizing a solution comprising about: 0.125 mg/mL of aPC and about 2.375 mg of PCZ; or about 0.25 mg/mL of aPC and about 2.25 mg of PCZ; or about 0.5 mg/mL of aPC and about 2.0 mg of PCZ; or about 0.75 mg/mL of aPC and about 1.75 mg of PCZ; or about 1.0 mg/mL of aPC and about 1.5 mg of PCZ; or about 1.25 mg/mL of aPC and about 1.25 mg of PCZ; or about 1.5 mg/mL of aPC and about 1.0 mg of PCZ; or about 1.75 mg/mL of aPC and about 0.75 mg of PCZ; or about 2.0 mg/mL of aPC and about 0.5 mg of PCZ; or about 2.25 mg/mL of aPC and about 0.25 mg of PCZ; or about 2.475 mg PCZ and about 0.25 mg aPC. The aPC and PCZ is combined with about 15 mg/mL sucrose, about 20 mg/mL NaCl, and a sodium citrate buffer having a pH greater than 5.5 but less than 6.5. Additionally, the stable lyophilized formulation of aPC/PCZ comprises lyophilizing a solution comprising about 5 mg/mL of aPC and PCZ (in a ratio of about 99% PCZ: 1% aPC and every ratio between 1 % PCZ: 99% aPC), about 30 mg/mL sucrose, about 38 mg/mL NaCl, and a citrate buffer having a pH greater than 5.5 but less than 6.5.

Freeze-Dry Microscopy is a useful technique in determining the collapse temperatures of the frozen solutions that are to be lyophilized. DSC is a useful technique in determining the glass-transition temperature (Tg') of the frozen solution. The collapse and glass-transition temperatures are especially helpful in predicting the upper temperature limits that can be safely used during the freeze-drying process. Results of Freeze-Drying Microscopy are complimentary to the glass-transition temperature of the Tg', values obtained by DSC. A collapse temperature above −40° C. is optimal for the sample to be processed in a conventional freeze-dryer.

TABLE 1

Freeze dry processing of aPC formulation matrices:

| Formulation Matrix | | | |
|---|---|---|---|
| aPC Conc. | Sucrose Conc. | NaCl Conc. | Collapse Temperature |
| 2.5 mg/mL | 15 mg/mL | 50 mM | −59° C. |
| 2.5 mg/mL | 15 mg/mL | 150 mM | −60° C. |
| 2.5 mg/mL | 15 mg/mL | 325 mM | −37° C. |
| 5.0 mg/mL | 30 mg/mL | 50 mM | −50° C. to −45° C. |
| 5.0 mg/mL | 30 mg/mL | 150 mM | −60° C. to −55° C. |
| 5.0 mg/mL | 30 mg/mL | 325 mM | −64° C. |
| 5.0 mg/mL | 30 mg/mL | 650 mM | −32° C. to −28° C. |

The ratio of aPC/PCZ to sucrose to sodium chloride (in 10 or 20 mM citrate buffer) is believed to be an important formulation variable affecting the collapse and glass-transition temperatures. To be processed in a conventional freeze-dryer, the sodium chloride concentration must be high enough (preferably 325 mM for 2.5 mg/mL aPC/PCZ and 650 mM for 5 mg/mL aPC/PCZ formulations) to cause the sodium chloride to crystallize-out during the freezing part of the freeze-drying process. Formulations of aPC/PCZ can be processed in a conventional freeze dryer to produce lyophilized products consisting of 1 part aPC/PCZ, 6 parts sucrose, and 7.6 parts sodium chloride by weight. One skilled in the art will now appreciate that PCZ may be formulated similarly to the Examples disclosed for aPC. The aPC:PCZ ratio combined is preferably about 1 part aPC and PCZ, to 6 parts sucrose, to about 7.6 parts sodium chloride by weight.

EXAMPLE 7

Stability of aPC in Product Formulations Containing Different Bulking Agents

Formulations of aPC were prepared to investigate the effect of various bulking agents on the stability of the molecule. A total of 6 excipients were added to aPC in phosphate buffer containing no salt. These bulking agents are glycine, mannitol, sucrose, trehalose, raffinose, and hydroxyethyl starch (HES). The stability of aPC in the phosphate, no salt, no bulking agent formulation ("control") was compared to that in the bulking agent formulations. Samples were stored at 50° C., 40° C., and 25° C. for various lengths of time. Data from analyses of these samples were compared to the initial values (time=0). APTT potency, size exclusion-high performance liquid chromatography (SE-HPLC), SDS-PAGE, and protein content assays were used to evaluate the physical and chemical stability of the formulations.

Formulations of aPC were prepared by dissolving aPC in phosphate buffer to 5 mg/mL aPC. Bulking agents were added to portions of the aPC solution at a ratio of 6:1 (bulking agents to aPC), or 30 mg/mL. The samples were lyophilized to 5 mg aPC/vial.

The formulations were put on stability at 50° C. for 14 and 28 days; 40° C. for 28 days, 48 days and 6 months; and 25°

C. for 6 and 12 months. For each time point, two vials of each formulation were analyzed independently as separate samples and data from these samples were compared to those from initial values (time=0). Analyses included aPC potency (APTT), SDS-PAGE, percent of aPC monomer, and protein content.

| | | 25° C. | | | control 50° C. | | | 40° C. | | |
|---|---|---|---|---|---|---|---|---|---|---|
| | Via | Initia | 6 mont | 12 month | Initi | 14 day | 28 day | Initi | 28 day | 84 day | 6 mont |
| APTT (U/mg) | 1 | 321 | 294 | 236 | 321 | 248 | 248 | 321 | 248 | 221 | 215 |
| | 2 | 321 | 251 | 242 | 321 | 245 | 227 | 321 | 279 | 233 | 176 |
| Monomer Content | 1 | 99.3 | 98.3 | 96.5 | 99.3 | 97.5 | 97.0 | 99.3 | 97.7 | 96.2 | 95.1 |
| | 2 | 99.2 | 95.8 | 96.4 | 99.2 | 97.3 | 97.1 | 99.2 | 97.7 | 96.1 | 95.4 |

| | | 25° C. | | | glycin 50° C. | | | 40° C. | | |
|---|---|---|---|---|---|---|---|---|---|---|
| | Via | Initi | 6 month | 12 month | Initi | 14 day | 28 day | Initi | 28 day | 84 day | 6 month |
| APTT (U/mg) | 1 | 282 | 233 | 142 | 282 | 164 | 97 | 282 | 191 | 155 | 158 |
| | 2 | 321 | 239 | 191 | 321 | 161 | 142 | 321 | 215 | 152 | 79 |
| Monomer Content | 1 | 99.1 | 98.4 | 93.3 | 99.1 | 97.4 | 97.2 | 99.1 | 97.8 | 96.4 | 95.8 |
| | 2 | 99.1 | 98.4 | 96.3 | 99.1 | 97.3 | 97.1 | 99.1 | 97.7 | 96.4 | 95.7 |

| | | 25° C. | | | mannitol | | | 40° C. | | |
|---|---|---|---|---|---|---|---|---|---|---|
| | Vial | Initial | 6 month | 12 month | Initial | 14 day | 28 day | Initial | 28 day | 84 day | 6 month |
| APTT (U/mg) | 1 | 309 | 227 | 255 | 309 | 270 | 245 | 309 | 273 | 270 | 282 |
| | 2 | 321 | 321 | 267 | 321 | 239 | 242 | 321 | 300 | 251 | 191 |
| Monomer Content | 1 | 99.2 | 98.8 | 97.4 | 99.2 | 98. | 98.1 | 99.2 | 98. | 97.6 | 97.8 |
| | 2 | 99.2 | 98.7 | 97.6 | 99.2 | 98. | 98.0 | 99.2 | 98. | 97.6 | 97.8 |

| | | 25° C. | | | Suc | | | 40° C. | | |
|---|---|---|---|---|---|---|---|---|---|---|
| | Vial | Initial | 6 month | 12 month | Initial | 14 day | 28 day | Initial | 28 day | 84 day | 6 month |
| APTT (U/mg) | 1 | 327 | 300 | 288 | 327 | 300 | 288 | 327 | 267 | 306 | 285 |
| | 2 | 297 | 300 | 306 | 297 | 291 | 291 | 297 | 321 | 242 | 294 |
| Monomer Content | 1 | 99.2 | 99.0 | 98.5 | 99.2 | 98. | 98.9 | 99.2 | 98. | 98.5 | 98.9 |
| | 2 | 99.2 | 99.0 | 98.5 | 99.2 | 98. | 98.9 | 99.2 | 98. | 98.5 | 98.9 |

| | | 25° C. | | | Trehalo 50° C. | | | 40° C. | | |
|---|---|---|---|---|---|---|---|---|---|---|
| | Via | Initi | 6 month | 12 month | Initi | 14 day | 28 day | Initi | 28 day | 84 day | 6 month |
| APTT (U/mg) | 1 | 312 | 291 | 282 | 312 | 258 | 282 | 312 | 273 | 276 | 276 |
| | 2 | 309 | 315 | 282 | 309 | 270 | 215 | 309 | 303 | 245 | 255 |
| Monomer Content | 1 | 99.2 | 99.0 | 98.4 | 99.2 | 98.6 | 98.8 | 99.2 | 98.8 | 98.4 | 98.7 |
| | 2 | 99.2 | 98.8 | 98.4 | 99.2 | 98.6 | 98.8 | 99.2 | 98.7 | 98.4 | 98.7 |

| | | 25° C. | | | raffinose 50° C. | | | 40° C. | | |
|---|---|---|---|---|---|---|---|---|---|---|
| | Via | Initi | 6 month | 12 month | Initi | 14 day | 28 day | Initi | 28 day | 84 day | 6 month |
| APTT (U/mg) | 1 | 321 | 270 | 255 | 321 | 261 | 258 | 321 | 276 | 273 | 279 |
| | 2 | 288 | 285 | 306 | 288 | 255 | 264 | 288 | 270 | 239 | 255 |
| Monomer Content | 1 | 99.1 | 99.0 | 97.0 | 99.1 | 98.6 | 98.7 | 99.1 | 98.7 | 98.4 | 98.6 |
| | 2 | 99.1 | 99.0 | 98.2 | 99.1 | 98.6 | 98.7 | 99.1 | 98.7 | 98.4 | 98.6 |

-continued

| | | 25° C. | | | HES 50° C. | | | 40° C. | | |
|---|---|---|---|---|---|---|---|---|---|---|
| | Via | Initi | 6 month | 12 month | Initi | 14 day | 28 day | Initi | 28 day | 84 day | 6 month |
| APTT | 1 | 282 | 188 | 176 | 282 | 182 | 164 | 282 | 194 | 185 | 145 |
| (U/mg) | 2 | 285 | 245 | 215 | 285 | 188 | 161 | 285 | 176 | 152 | 103 |
| Monomer | 1 | 97.8 | 95.6 | 92.2 | 97.8 | 93.0 | 91.8 | 97.8 | 93.7 | 90.6 | 88.7 |
| Content | 2 | 97.8 | 95.3 | 91.8 | 97.8 | 92.9 | 91.0 | 97.8 | 92.9 | 90.5 | 88.5 |

There were no significant changes in pH, color, package characteristics and physical appearance for any of the samples over the one year stability time period. When analyzed by the APTT and SE-HPLC procedures, the HES and glycine formulation had less physical stability (through aggregation) and chemical stability (potency) when compared to the control. The mannitol formulation offered slightly better physical and chemical stability than the control, and the remaining formulations, sucrose, trehalose and raffinose, all demonstrated even more superior physical and chemical stability when compared to the control. Therefore, mannitol, sucrose, trehalose and raffinose, as bulking agents in aPC formulations, offer increased chemical and physical stability when compared to an aPC formulation without a bulking agent or those having glycine or HES. Albumin or a similar known pharmaceutical excipients may be added, for example, to improve stability.

EXAMPLE 8

Stability of Recombinant Human APC

Two lots of a lyophilized formulation of recombinant human aPC were stored for 1 month at 40° C./75% relative humidity, and then analyzed for possible degradation. The stability of aPC was also monitored after reconstitution with sterile water and storage for up to 72 hours at ambient temperature. The lyophilized aPC product consisted of 10 mg aPC, 60 mg sucrose, 76 mg sodium chloride, and 15.1 mg citrate per vial. The aPC in this formulation is stable in the dry state for at least 1 month when stored at 40° C./75% relative humidity, and in solution for 24 hours when stored at ambient temperature.

Both lots were prepared using the same unit formula of 10 mg aPC, 60 mg sucrose, 76 mg sodium chloride, and 15.1 mg citrate per vial. Both lyophilized lots of aPC were stored for 1 month at 40° C./75% relative humidity and the stability of aPC was monitored using the APTT potency assay, ion-pairing HPLC for quantitation of aPC peptides and mass spectrometry for quantitation of protein variant forms. One lot was also reconstituted with sterile water, to 1 mg/mL aPC, and held at ambient temperature. The stability of aPC in solution was monitored at the 0, 1, 4, 8, 24, 48 and 72 hour time points using the APTT and mass spectrometry methods.

There was no loss of aPC activity and an insignificant amount of structural degradation of the molecule after storage in the dry state for one month at 40° C./75% relative humidity. The aPC in this formulation is stable for up to 24 hours at about 1 mg/mL to about 4 mg/mL after reconstitution.

We claim:

1. A method of treating a human patient with a hypercoagulable state or protein C deficiency which comprises administering to said patient activated Protein C (aPC) and protein C zymogen (PCZ).

2. The method according to claim 1 wherein said hypercoagulable state or protein C deficiency is associated with a disease or condition selected from: sepsis, severe sepsis, septic shock, disseminated intravascular coagulation, purpura fulminans, major trauma, undergoing or recovering from surgery, burns, adult respiratory distress syndrome, bone marrow and other organ transplantations, deep vein thrombosis, heparin-induced thrombocytopenia, sickle cell disease, thalassemia, viral hemorrhagic fever, thrombotic thrombocytopenic purpura, hemolytic uremic syndrome, unstable angina, myocardial infarction, meningococcemia, melioidosis, complications during pregnancy, preeclampsia, eclampsia, amniotic fluid embolism, placental abruption, and chemotherapy.

3. The method of claim 2 wherein the hypercoagulable state or protein C deficiency is selected from sepsis, severe sepsis, and septic shock.

4. The method of any of claims 1 to 3 wherein the activated Protein C is administered to the patient first, followed by administration of protein C zymogen.

5. The method of any of claims 1 to 3 wherein the protein C zymogen is administered to the patient first, followed by administration of activated Protein C.

6. The method of any of claims 1 to 3 wherein the activated Protein C and protein C zymogen are administered simultaneously to the patient.

7. The method of any of claims 1 to 3 wherein the administration of the activated Protein C and protein C zymogen is alternated back and forth between the activated Protein C and the protein C zymogen.

8. The method of any of claims 1 to 3 wherein the activated Protein C is administered by continuous infusion at a dose of about 1 µg/kg/hr to about 50 µg/kg/hr.

9. The method of any of claims 1 to 3 wherein the activated Protein C is administered by continuous infusion at a dose of about 5 µg/kg/hr to about 30 µg/kg/hr.

10. The method of any of claims 1 to 3 wherein the activated Protein C is administered by continuous infusion at a dose of about 5 µg/kg/hr to about 25 µg/kg/hr.

11. The method of any of claims 1 to 3 wherein the activated Protein C and the protein C zymogen are administered to achieve an aPC plasma range of about 20 ng/ml to about 160 ng/ml.

12. The method of claim 11 wherein the activated Protein C plasma range is about 25 ng/ml to about 100 ng/ml.

13. The method of claim 8, wherein the dose of protein C zymogen is about 60 to about 120 µg/kg/day with or without a bolus of about 100 to about 500 µg/kg.

14. The method of claim 13, wherein the dose of PCZ is about 90 μg/kg/day with or without a bolus of about 100 to about 500 μg/kg.

15. The method of claim 2 or claim 3, wherein the aPC and/or the PCZ are produced recombinantly.

16. The method of claim 2 or claim 3, wherein the aPC and/or the PCZ are plasma derived.

17. A pharmaceutical formulation which comprises activated Protein C, protein C zymogen, and a pharmaceutical carrier wherein the weight:weight ratio of the activated Protein C and the protein C zymogen is selected from: 5% by weight protein C zymogen: 95% by weight activated Protein C; 10% by weight protein C zymogen: 90% by weight activated Protein C; 15% by weight protein C zymogen: 85% by weight activated Protein C; 20% by weight protein C zymogen: 80% by weight activated Protein C; 25% by weight protein C zymogen: 75% by weight activated Protein C; 30% by weight protein C zymogen: 70% by weight activated Protein C; 35% by weight protein C zymogen: 65% by weight activated Protein C; 40% by weight protein C zymogen: 60% by weight activated Protein C; 45% by weight protein C zymogen: 55% by weight activated Protein C; and 50% by weight protein C zymogen: 50% by weight activated Protein C; 60% by weight protein C zymogen: 40% by weight activated Protein C; 70% by weight protein C zymogen: 30% by weight activated Protein C; 80% by weight protein C zymogen: 20% by weight activated Protein C; 90% by weight protein C zymogen: 10% by weight activated Protein C; 95% by weight protein C zymogen: 5% by weight activated Protein C; and 99% by weight protein C zymogen: 1% by weight activated Protein C.

18. The formulation of claim 17 wherein the ratio is: 5% by weight protein C zymogen: 95% by weight activated Protein C.

19. The formulation of claim 17 wherein the ratio is: 10% by weight protein C zymogen: 90% by weight activated Protein C.

20. The formulation of claim 17 wherein the ratio is: 15% by weight protein C zymogen: 85% by weight activated Protein C.

21. The formulation of claim 17 wherein the ratio is: 20% by weight protein C zymogen: 80% by weight activated Protein C.

22. The formulation of claim 17 wherein the ratio is: 25% by weight protein C zymogen: 75% by weight activated Protein C.

23. The formulation of claim 17 wherein the ratio is: 30% by weight protein C zymogen: 70% by weight activated Protein C.

24. The formulation of claim 17 wherein the ratio is: 35% by weight protein C zymogen: 65% by weight activated Protein C.

25. The formulation of claim 17 wherein the ratio is: 40% by weight protein C zymogen: 60% by weight activated Protein C.

26. The formulation of claim 17 wherein the ratio is: 45% by weight protein C zymogen: 55% by weight activated Protein C.

27. The formulation of claim 17 wherein the ratio is: 50% by weight protein C zymogen: 50% by weight activated Protein C.

28. The formulation of claim 17 wherein the ratio is: 55% by weight protein C zymogen: 45% by weight activated Protein C.

29. The formulation of claim 17 wherein the ratio is: 60% by weight protein C zymogen: 40% by weight activated Protein C.

30. The formulation of claim 17 wherein the ratio is: 65% by weight protein C zymogen: 35% by weight activated Protein C.

31. The formulation of claim 17 wherein the ratio is: 70% by weight protein C zymogen: 30% by weight activated Protein C.

32. The formulation of claim 17 wherein the ratio is: 75% by weight protein C zymogen: 25% by weight activated Protein C.

33. The formulation of claim 17 wherein the ratio is: 80% by weight protein C zymogen: 20% by weight activated Protein C.

34. The formulation of claim 17 wherein the ratio is: 85% by weight protein C zymogen: 15% by weight activated Protein C.

35. The formulation of claim 17 wherein the ratio is: 90% by weight protein C zymogen: 10% by weight activated Protein C.

36. The formulation of claim 17 wherein the ratio is: 95% by weight protein C zymogen: 5% by weight activated Protein C.

37. The formulation of claim 17 wherein the ratio is: 99% by weight protein C zymogen: 1% by weight activated Protein C.

* * * * *